(12) United States Patent
Crooks et al.

(10) Patent No.: US 8,124,652 B2
(45) Date of Patent: *Feb. 28, 2012

(54) USE OF PARTHENOLIDE DERIVATIVES AS ANTILEUKEMIC AND CYTOTOXIC AGENTS

(75) Inventors: Peter A. Crooks, Nicholasville, KY (US); Craig T. Jordan, Rochester, NY (US); Xiaochen Wei, Lexington, KY (US)

(73) Assignee: University of Kentucky, Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/693,161

(22) Filed: Jan. 25, 2010

(65) Prior Publication Data

US 2010/0184745 A1    Jul. 22, 2010

Related U.S. Application Data

(60) Division of application No. 11/031,315, filed on Jan. 7, 2005, now Pat. No. 7,678,904, which is a continuation-in-part of application No. 10/888,274, filed on Jul. 9, 2004, now Pat. No. 7,312,242.

(60) Provisional application No. 60/486,171, filed on Jul. 11, 2003.

(51) Int. Cl.
*A01N 43/16* (2006.01)
*C07D 405/00* (2006.01)
*C07D 409/00* (2006.01)

(52) U.S. Cl. .................. 514/456; 548/526; 544/378
(58) Field of Classification Search .............. 514/456; 548/526; 544/378
See application file for complete search history.

(56) References Cited

U.S. PATENT DOCUMENTS 6,462,204 B2   10/2002   Hall et al.
(Continued)

FOREIGN PATENT DOCUMENTS
GB      2124486 A      1/1984
(Continued)

OTHER PUBLICATIONS

U.S. Appl. No. 60/459,769, filed Apr. 2, 2003, Hsieh et al.
(Continued)

*Primary Examiner* — Nizal Chandrakumar
(74) *Attorney, Agent, or Firm* — Akerman Senterfitt

(57) ABSTRACT

The present invention provides compounds of the formula (I)

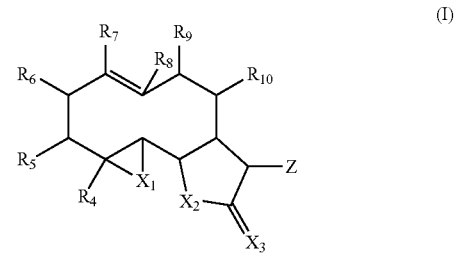

(I)

wherein:
$X_1$, $X_2$ and $X_3$ are heteroatoms;
$R_4$, $R_5$, $R_6$, $R_7$, $R_8$, $R_9$ and $R_{10}$ are independently selected from H, halo, —OH, —NO$_2$, —CN and optionally substituted aliphatic, cycloalkyl, heterocycloalkyl, aryl or heteroaryl; and
Z is optionally substituted $C_{1-8}$ straight-chained or branched aliphatic, optionally containing 1 or more double or triple bonds, wherein one or more carbons are optionally replaced by R* wherein R* is optionally substituted cycloalkyl, heterocycloalkyl, aryl or heteroaryl; an amino acid residue, H, —CN, —C(O)—, —C(O)C(O)—, —C(O)NR$^1$—, —C(O)NR$^1$NR$^2$—, —C(O)O—, —OC(O)—, —NR$^1$CO$_2$—, —O—, —NR$^1$C(O)NR$^2$—, —OC(O)NR$^1$—, —NR$^1$NR$^2$—, —NR$^1$C(O)—, —S—, —SO—, —SO$_2$—, —NR$^1$—, —SO$_2$NR$^1$—, —NR$^1$R$^2$, or —NR$^1$SO$_2$—, wherein R$^1$ and R$^2$ are independently selected from H and optionally substituted aliphatic, cycloalkyl, heterocycloalkyl, aryl or heteroaryl; or where R* is NR$^1$R$^2$, R$^1$ and R$^2$ optionally together with the nitrogen atom form an optionally substituted 5-12 membered ring, said ring optionally comprising 1 or more heteroatoms or a group selected from —CO—, —SO—, —SO$_2$— and —PO—; or
a pharmaceutically acceptable salt, ester or prodrug thereof.

43 Claims, 12 Drawing Sheets

U.S. PATENT DOCUMENTS

| | | | |
|---|---|---|---|
| 6,890,946 | B2 | 5/2005 | Nakshatri |
| 7,312,242 | B2 * | 12/2007 | Crooks et al. ............ 514/456 |
| 7,678,904 | B2 * | 3/2010 | Crooks et al. ............ 544/153 |
| 2004/0229936 | A1 | 11/2004 | Hsieh |

FOREIGN PATENT DOCUMENTS

| | | |
|---|---|---|
| JP | 59001425 | 1/1984 |
| JP | 2002-509532 T | 3/2002 |
| WO | WO 98/48789 | 11/1998 |
| WO | WO 01/45699 | 6/2001 |
| WO | WO 02/40017 | 5/2002 |
| WO | WO 02/055523 | 7/2002 |

OTHER PUBLICATIONS

Allen et al. (1964) Can. J. Chem. 42:2616-2620 "The Thermal Reversibility of the Michael Reaction".

Calvet et al. (2002) ARKIVOC 189-195, "Diastereoselective thiol conjugate addition on δ-alkylated-γ-silylated-α, β-unsaturated-δ-lactones".

Cory and Cory (2001) Anticancer Research 21:3807-11 "Augmentation of apoptosis responses in p53-deficient L1210 cells by compounds directed at blocking NFkappaB activation".

Cory and Cory (2002) Anticancer Research 22:3805-9 "Lactacystin, a proteasome inhibitor, potentiates the apoptotic effect of parthenlolide, an inhibitor of NFkappaB activation, on drug-resistant mouse leukemia L1210 cells".

European Supplementary Search Report dated Dec. 29, 2008 in related European Patent Application 04777849.3.

Gelfanov et al. (2000) Blood 98:2508-17 "Transformation of interleukin-3-dependent cells without participation of Stat5/bcl-xL: cooperation of akt with aft/erk leads to p65 nuclear factor κB-mediated antiapoptosis involving c-IAP2".

Hejchman et al. (1995) J. Med. Chem. 38:3407-3410 "Synthesis and Cytotoxicity of Water-Soluble Ambrosin Prodrug Candidates".

Hwang et al. (1996) STN Accession No. 1996:592356, Abstract of Biochemical and Biophysical Research Communications 226(3):810-818 "Inhibition of the expression of inducible cyclooxygenase lactones in macrophages correlates with the inhibition of MAP kinases".

Hwang et al. (2006) Bioorganic and Medicinal Chemistry 14:83-91 "Synthesis and anti-viral activity of a series of sesquiterpene lactones and analogues in the subgenomic HCV replicon system".

Jha and Joshi (2002) ARKIVOC 2002(vii) 167-196 "Catalytic, enatioselective Michael addition reactions".

Kang et al. (2002) Brit. J. Pharmacol. 135:1235-44 "Enhancement of 1α,25-dihydroxyvitamin $D_3$-induced differentiation of human leukaemia HL-60 cells into monocytes by parthenolide via inhibition of NF-κB activity".

Martinelli et al. (2002) Tetrahedron Letters 43:3365-3367 "Reaction of cryptophycin 52 with thiols".

Neelakantan, et al. (2009) Bioorganic & Medicinal Chemistry Letters "Aminoparthenolides as novel anti-leukemic agents: discovery of the NF-κB inhibitor, DMAPT (LC-1)" preprint of approved article to be published in 2009.

Ruangrungsi et al. (1987) J. of Natural Products 50(5):891-896 "Constituents of Paramichelia Baillonii: a New Antitumor Germacranolide Alkaloid".

Ruangrungsi et al. (1988) J. of Natural Products 51(6):1220-1225 "Constituents of Michelia Rajaniana. Two new germacranoloide amides".

Song et al. (2001) J. Asian. Nat. Prod. Res. 3:385-91 "A new sesquiterpene lactone from Tsoongiodendron odorum chun".

Wen et al. (2002) J. Biol. Chem. 277:38954-38964 "Oxidative stress-mediated apoptosis".

Wu et al. (2001) STN Accession No. 2001:506624, Abstract of Journal of Asian Natural Products Research 3(2):95-102 "Two new germacranolides from *Magnolia grandiflora*".

Abduazimov B.Kh et al. (1986) Khimiko-Farmatsevticheskii Zhurnal 20(12):1451-54 "Synthesis and antitumor activity of the lactine amorolid". (Summary in English).

Abduazimov, BK et al. (1997) Chemistry of Natural Compounds 33(5):554-57 "Modification of the Sesquiterpene Lactone Arteannuin B and Antimicrobial Activities of the Products Obtained".

Kuo-Hsiung Lee et al. (1972) Journal of Medicinal Chemistry 15(6):609-11 "Antitumor agents.3 Synthesis and cytotoxic activity of helenalin amine adducts and relate derivates".

Ross, JJ et al. (1999) PMID: 10193202 "Low concentration of the feverfew component parthenolide inhibit in vitro growth of tumor lines in a cytostatic fashion".

* cited by examiner

USE OF PARTHENOLIDE DERIVATIVES AS ANTILEUKEMIC AND CYTOTOXIC AGENTS

This is a divisional application of U.S. patent application Ser. No. 11/031,315 filed Jan. 7, 2005, now U.S. Pat. No. 7,678,904, which is a continuation-in-part of U.S. patent application Ser. No. 10/888,274 filed Jul. 9, 2004, now U.S. Pat. No. 7,312,242, which claims the benefit of priority to provisional application No. 60/486,171 filed Jul. 11, 2003.

FIELD OF THE INVENTION

The present invention relates to methods for the structural modification of the sesquiterpene lactone, parthenolide, and the use of these parthenolide derivatives in the treatment of carcinoma. More specifically, the invention relates to the methods to prepare structural analogs of the parent compound, parthenolide, in order to obtain new, pharmacologically active chemical entities with improved water solubility characteristics, and to use them in the treatment of leukemias and other parental and multi-drug resistant cancers

BACKGROUND OF THE INVENTION

Sesquiterpene lactones are a group of secondary plant metabolites consisting of a 15-carbon structure containing an α-methylene-γ-butyrolactone moiety and other additional functional groups. Over the last two to three decades, these terpenoids have received considerable attention due to the broad spectrum of their biological activities, to the plants which produce them, and most importantly, because of their pharmacological effects in humans. About 4,000 of these terpenoids have been isolated and identified, most of them in *Asteraceae* (Compositae, sunflower family) (Schmidt, *Curr. Org. Chem.* 1999, 3, 577-608). Some of these plants have been used for centuries in indigenous medical practices in various cultures worldwide.

Parthenolide (1) is a Germacrane sesquiterpene lactone with a unique structure. It has been isolated from several different species in *Asteraceae* (Compositae) family, feverfew (*Tanacetum parthenium*) being one of them.

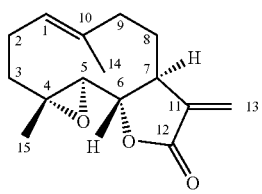

Feverfew has been used to reduce fever and pain and in the treatment of migraine and rheumatoid arthritis (Heptinstall et al., ACS Symposium Series (1998), 691 (Phytomedicines of Europe), 158-175.). The active component is parthenolide (1). Recently, it has been revealed that parthenolide (1) can induce tumor apoptosis by the inhibition of NF-κB activities (Cory et al., *Anticancer Research* 2002, 22, 3805-9; Cory et al., *Anticancer Research* 2001, 21, 3807-11; Gelfanov et al., *Blood,* 2000, 98, 2508-17; Kang et al, *Brit. J. Pharmacol.* 2002, 135, 1235-44; Song et al., *J. Asian. Nat. Prod. Res.* 2001, 3, 285-91).

Parthenolide (1) is a lipophilic, neutral lactone with low polarity, and has a low water-solubility, limiting its development as a therapeutic agent. Thus, a need exists for the development of soluble parthenolide derivatives that retain their anti-cancer activity.

SUMMARY OF THE INVENTION

In accordance with the present invention, a novel class of compounds with antileukemic activity is presented. Accordingly, the present invention provides compounds of formula (I):

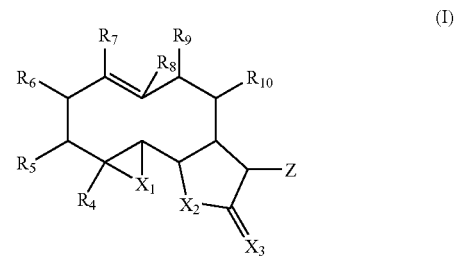

wherein:
$X_1$, $X_2$ and $X_3$ are heteroatoms;
$R_4$, $R_5$, $R_6$, $R_7$, $R_8$, $R_9$ and $R_{10}$ are independently selected from H, halo, —OH, —NO$_2$, —CN and optionally substituted aliphatic, cycloalkyl, heterocycloalkyl, aryl or heteroaryl; and
Z is optionally substituted $C_{1-8}$ straight-chained or branched aliphatic, optionally containing 1 or more double or triple bonds, wherein one or more carbons are optionally replaced by R* wherein R* is optionally substituted cycloalkyl, heterocycloalkyl, aryl or heteroaryl; an amino acid residue, H, —CN, —C(O)—, —C(O)C(O)—, —C(O)NR$^1$—, —C(O)NR$^1$NR$^2$—, —C(O)O—, —OC(O)—, —NR$^1$CO$_2$—, —O—, —NR$^1$C(O)NR$^2$—, —OC(O)NR$^1$—, —NR$^1$NR$^2$—, —NR$^1$C(O)—, —S—, —SO—, —SO$_2$—, —NR$^1$—, —SO$_2$NR$^1$—, —NR$^1$R$^2$, or —NR$^1$SO$_2$—, wherein R$^1$ and R$^2$ are independently selected from H and optionally substituted aliphatic, cycloalkyl, heterocycloalkyl, aryl or heteroaryl; or where R* is NR$^1$R$^2$, R$^1$ and R$^2$ optionally together with the nitrogen atom form an optionally substituted 5-12 membered ring, said ring optionally comprising 1 or more heteroatoms and/or a group selected from —CO—, —SO—, —SO$_2$— and —PO—; or
a pharmaceutically acceptable salt, ester or prodrug thereof.

The invention also provides a pharmaceutical composition comprising an effective amount of a compound of formula (I), or a pharmaceutically acceptable salt, ester or prodrug thereof, in combination with a pharmaceutically acceptable diluent or carrier.

The invention also provides a method of inhibiting cancer cell growth and metastasis of cancer cells, comprising administering to a mammal afflicted with cancer, an amount of a compound of formula (I), effective to inhibit the growth of said cancer cells.

The invention also provides a method comprising inhibiting cancer cell growth by contacting said cancer cell in vitro or in vivo with an amount of a compound of formula (I), effective to inhibit the growth of said cancer cell.

The invention also provides a compound of formula (I) for use in medical therapy (preferably for use in treating cancer, e.g. solid tumors), as well as the use of such compound for the manufacture of a medicament useful for the treatment of cancer and other diseases/disorders described herein.

The invention further provides methods of treating inflammatory diseases and disorders, including, for example, rheumatoid arthritis, osteoarthritis, allergies (such as asthma), and other inflammatory conditions, such as pain (such as migraine), swelling, fever, psoriasis, inflammatory bowel disease, gastrointestinal ulcers, cardiovascular conditions, including ischemic heart disease and atherosclerosis, partial brain damage caused by stroke, skin conditions (eczema, sunburn, acne), leukotriene-mediated inflammatory diseases of lungs, kidneys, gastrointestinal tract, skin, prostatitis and paradontosis.

The invention further provides methods of treating immune response disorders, whereby the immune response is inappropriate, excessive or lacking. Such disorders include allergic responses, transplant rejection, blood transfusion reaction, and autoimmune disorders such as systemic lupus erythematosus and rheumatoid arthritis.

DETAILED DESCRIPTION OF THE INVENTION

Figure 1:
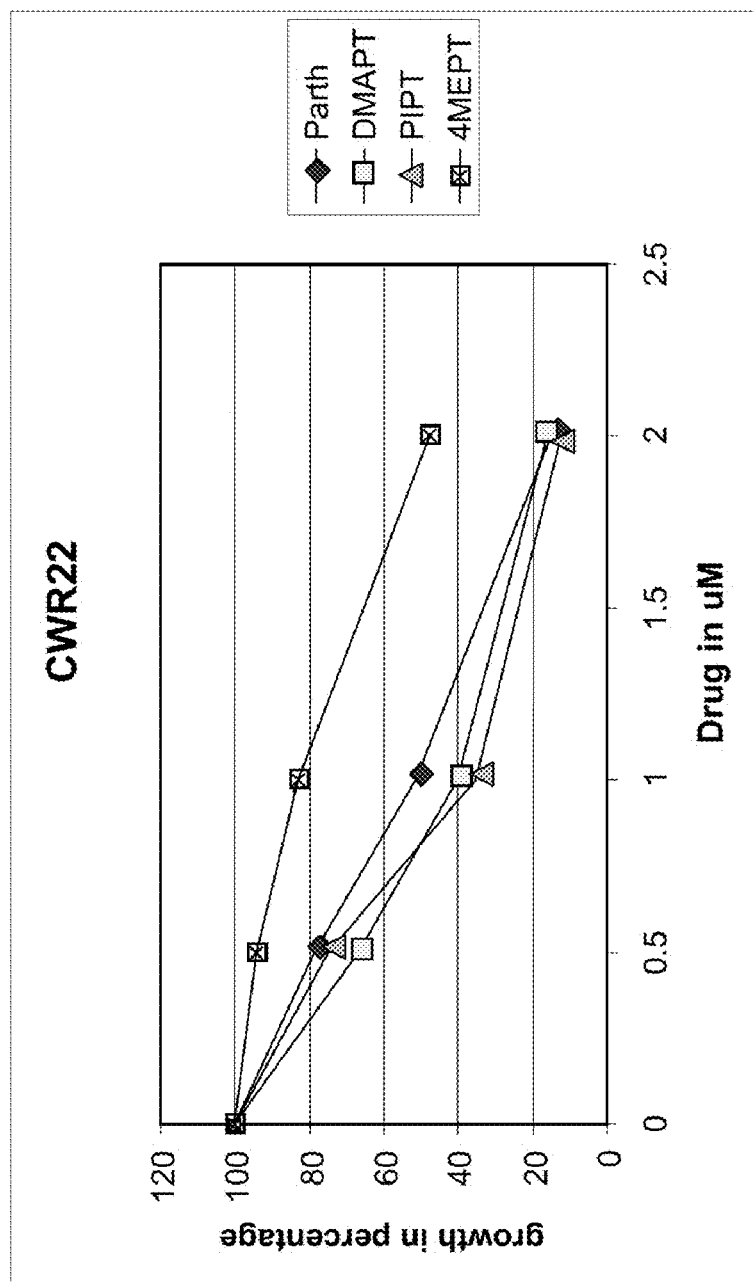
FIG. 1 shows the effectiveness of parthenolide and derivatives of the present invention against prostate cancer cell line CWR22 in a clonogenic assay.
Figure 2:
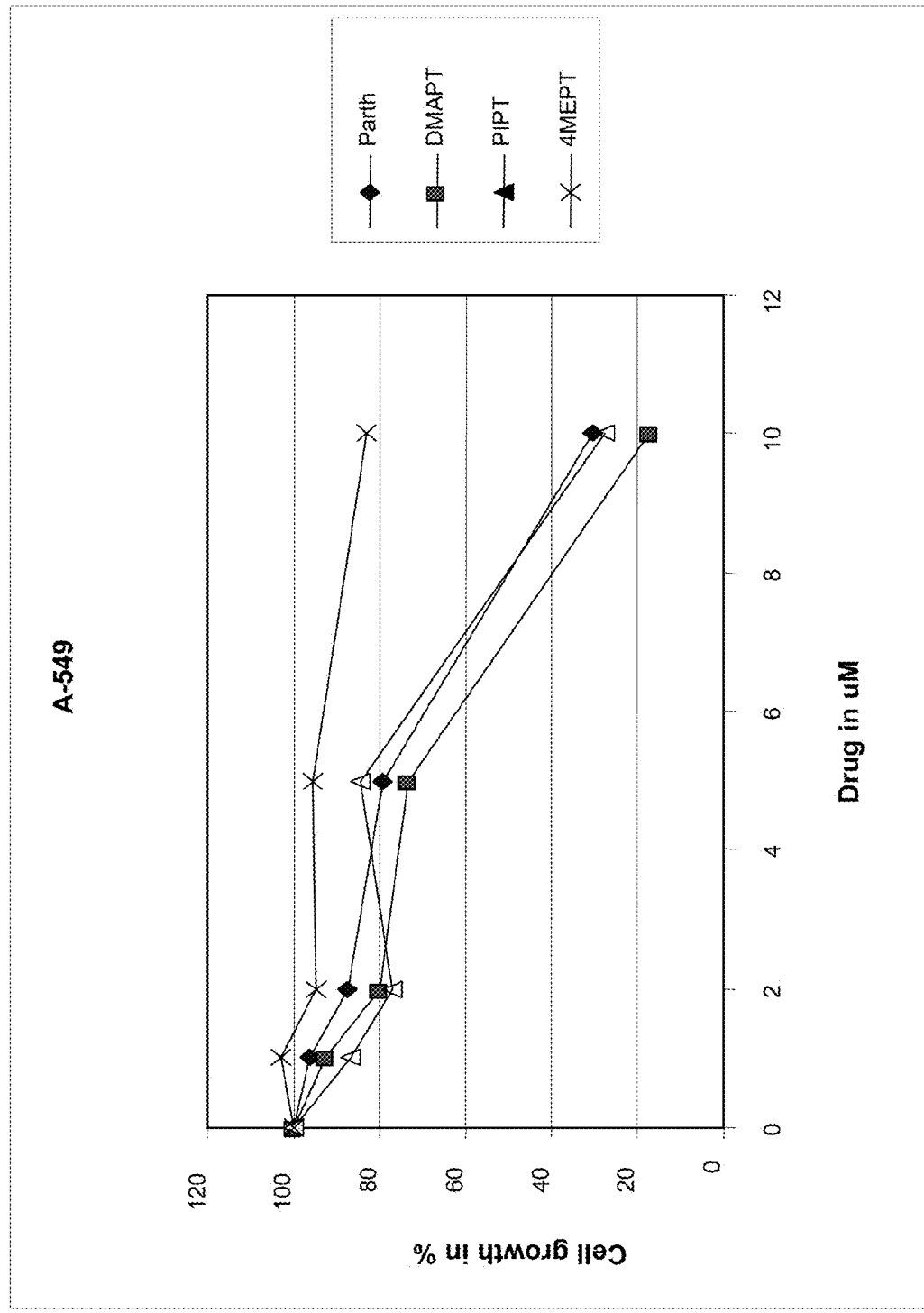
FIG. 2 shows the effectiveness of parthenolide and derivatives of the present invention against lung cancer cell line A-549 in a cellular proliferation MTS-PMS assay.
Figure 3:
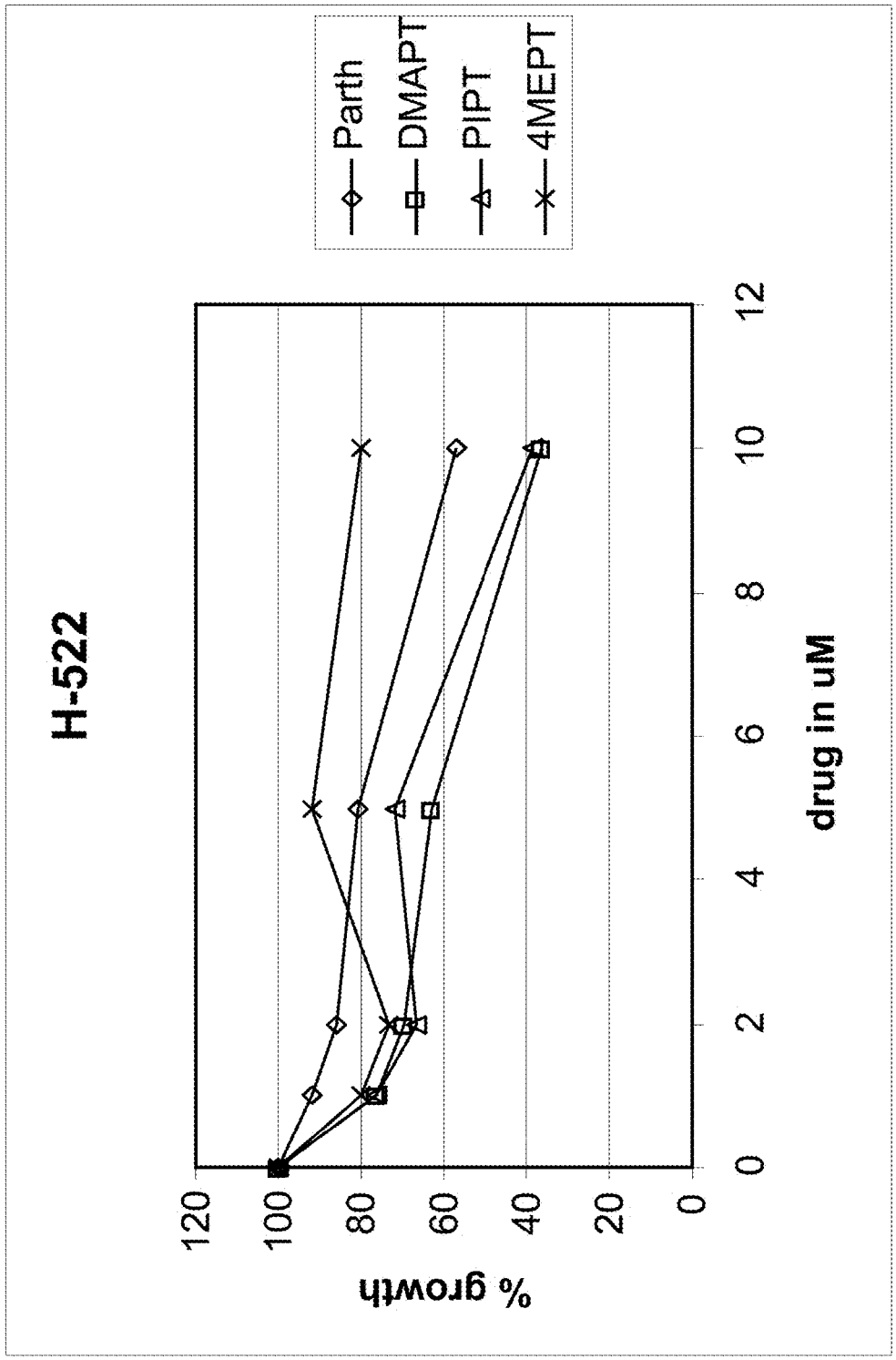
FIG. 3 shows the effectiveness of parthenolide and derivatives of the present invention against lung cancer cell line H-522 in a cellular proliferation MTS-PMS assay.

As used herein, the following definitions shall apply unless otherwise indicated.

The phrase "optionally substituted" is used interchangeably with the phrase "substituted or unsubstituted." Unless otherwise indicated, an optionally substituted group may have a substituent at each substitutable position of the group, and each substitution is independent of any other. Also, combinations of substituents or variables are permissible only if such combinations result in stable compounds. In addition, unless otherwise indicated, functional group radicals are independently selected. Where "optionally substituted" modifies a series of groups separated by commas (e.g., "optionally substituted A, B or C"; or "A, B or C optionally substituted with"), it is intended that each of the groups (e.g., A, B and C) is optionally substituted.

The term "aliphatic" or "aliphatic group" as used herein means a straight-chain or branched $C_{1-12}$ hydrocarbon chain that is completely saturated or that contains one or more units of unsaturation, or a monocyclic $C_{3-8}$ hydrocarbon or bicyclic $C_{8-12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl," "alkoxy," "hydroxyalkyl," "alkoxyalkyl" and "alkoxycarbonyl," used alone or as part of a larger moiety include both straight and branched chains containing one to twelve carbon atoms. The terms "alkenyl" and "alkynyl" used alone or as part of a larger moiety shall include both straight and branched chains containing two to twelve carbon atoms.

The terms "haloalkyl," "haloalkenyl" and "haloalkoxy" means alkyl, alkenyl or alkoxy, as the case may be, substituted with one or more halogen atoms. The term "halogen" or "halo" means F, Cl, Br or I.

The term "heteroatom" means nitrogen, oxygen, or sulfur and includes any oxidized form of nitrogen and sulfur, and the quaternized form of any basic nitrogen. Heteroatom further includes Se, Si and P.

The term "aryl" used alone or in combination with other terms, refers to monocyclic, bicyclic or tricyclic carbocyclic ring systems having a total of five to fourteen ring members, wherein at least one ring in the system is aromatic and wherein each ring in the system contains 3 to 8 ring members. The term "aryl" may be used interchangeably with the term "aryl ring". The term "aralkyl" refers to an alkyl group substituted by an aryl. The term "aralkoxy" refers to an alkoxy group substituted by an aryl.

The term "heterocycloalkyl," "heterocycle," "heterocyclyl" or "heterocyclic" as used herein means monocyclic, bicyclic or tricyclic ring systems having five to fourteen ring members in which one or more ring members is a heteroatom, wherein each ring in the system contains 3 to 7 ring members and is non-aromatic.

The term "heteroaryl," used alone or in combination with other terms, refers to monocyclic, bicyclic and tricyclic ring systems having a total of five to fourteen ring members, and wherein: 1) at least one ring in the system is aromatic; 2) at least one ring in the system contains one or more heteroatoms; and 3) each ring in the system contains 3 to 7 ring members. The term "heteroaryl" may be used interchangeably with the term "heteroaryl ring" or the term "heteroaromatic". Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. The term "heteroaralkyl" refers to an alkyl group substituted by a heteroaryl. The term "heteroarylalkoxy" refers to an alkoxy group substituted by a heteroaryl. \

An aryl (including aralkyl, aralkoxy, aryloxyalkyl and the like) or heteroaryl (including heteroaralkyl, heteroarylalkoxy and the like) group may contain one or more substituents. Suitable substituents on an unsaturated carbon atom of an aryl, heteroaryl, aralkyl or heteroaralkylgroup are selected from halogen; haloalkyl; —$CF_3$; —R; —OR; —SR; 1,2-methylenedioxy; 1,2-ethylenedioxy; protected OH (such as acyloxy); phenyl (Ph); Ph substituted with R; —O(Ph); —O—(Ph) substituted with R; —$CH_2$ (Ph); —$CH_2$ (Ph) substituted with R; —$CH_2CH_2$ (Ph); —$CH_2CH_2$ (Ph) substituted with R; —$NO_2$; —CN; —$N(R)_2$; —NRC(O)R; —NRC(O)N$(R)_2$; —$NRCO_2R$; —NRNRC(O)R; —NR—NRC(O)N$(R)_2$; —$NRNRCO_2R$; —C(O)C(O)R; —C(O)$CH_2$C(O)R; —$CO_2R$; —C(O)R; —C(O)$N(R)_2$; —OC(O)$N(R)_2$; —S(O)$_2R$; —$SO_2N(R)_2$; —S(O)R; —$NRSO_2N(R)_2$; —$NRSO_2R$; —C(=S)$N(R)_2$; —C(=NH)—$N(R)_2$; —$(CH_2)_y$NHC(O)R; —$(CH_2)_y$NHC(O)NHR; —$(CH_2)_y$NHC(O)OR; —$(CH_2)_y$NHS(O)R; —$(CH_2)_y$NHSO$_2$R; or —$(CH_2)_y$NHC(O)CH((V)$_z$—R)(R) wherein each R is independently selected from hydrogen, optionally substituted $C_{1-6}$ aliphatic, an unsubstituted 5-6 membered heteroaryl or heterocyclic ring, phenyl (Ph), —O(Ph), or —$CH_2$ (Ph)—$CH_2$ (Ph), wherein y is 0-6; z is 0-1; and V is a linker group. When R is $C_{1-6}$ aliphatic, it may be substituted with one or more substituents selected from —$NH_2$, —NH($C_{1-4}$ aliphatic), —N($C_{1-4}$ aliphatic)$_2$, —S(O)($C_{1-4}$ aliphatic), —$SO_2$ ($C_{1-4}$ aliphatic), halogen, ($C_{1-4}$ aliphatic), —OH, —O($C_{1-4}$ aliphatic), —$NO_2$, —CN, —$CO_2H$, —$CO_2$ ($C_{1-4}$ aliphatic), —O(halo $C_{1-4}$ aliphatic), or -halo ($C_{1-4}$ aliphatic); wherein each $C_{1-4}$ aliphatic is optionally.

An aliphatic group or a non-aromatic heterocyclic ring may contain one or more substituents. Suitable substituents on a saturated carbon of an aliphatic group or of a non-aromatic heterocyclic ring are selected from those listed above for the unsaturated carbon of an aryl or heteroaryl group and the following: =O, =S, =NNHR, =NN$(R)_2$, =N—, =NNHC(O)R, =NNHCO$_2$ (alkyl), =NNHSO$_2$ (alkyl), or =NR, where each R is independently selected from hydrogen or an optionally substituted $C_{1-6}$ aliphatic. When R is $C_{1-6}$ aliphatic, it may be substituted with one or more substituents selected from —$NH_2$, —NH($C_{1-4}$ aliphatic), —N($C_{1-4}$ aliphatic)$_2$, halogen, —OH, —O—($C_{1-4}$ aliphatic), —$NO_2$, —CN, —$CO_2H$, —$CO_2$ ($C_{1-4}$ aliphatic), —O(halo $C_{1-4}$ aliphatic), or -halo($C_{1-4}$ aliphatic); wherein each $C_{1-4}$ aliphatic is optionally substituted.

Substituents on a nitrogen of a non-aromatic heterocyclic ring are selected from —R, —$N(R)_2$, —C(O)R, —C(O)OR, —C(O)C(O)R, —C(O)$CH_2$C(O)R, —$SO_2R$, —$SO_2N(R)_2$, —C(=S)$N(R)_2$, —C(=NH)—$N(R)_2$ or —$NRSO_2R$; wherein each R is independently selected from hydrogen, an optionally substituted $C_{1-6}$ aliphatic, optionally substituted phenyl (Ph), optionally substituted —O(Ph), optionally substituted —$CH_2$ (Ph), optionally substituted —$CH_2CH_2$ (Ph), or an unsubstituted 5-6 membered heteroaryl or heterocyclic ring. When R is a $C_{1-6}$ aliphatic group or a phenyl ring, it may be substituted with one or more substituents selected from —$NH_2$, —NH($C_{1-4}$ aliphatic), —N($C_{1-4}$ aliphatic)$_2$, halogen, —($C_{1-4}$ aliphatic), —OH, —O—($C_{1-4}$ aliphatic), —$NO_2$, —CN, —$CO_2H$, —$CO_2$ ($C_{1-4}$ aliphatic), —O(halo $C_{1-4}$ aliphatic) or -halo($C_{1-4}$ aliphatic); wherein each $C_{1-4}$ aliphatic is optionally substituted.

The term "linker group" or "linker" means an organic moiety that connects two parts of a compound. Linkers include alkylidene chain that is a saturated or unsaturated, straight or branched, $C_{1-8}$ carbon chain which is optionally substituted, and wherein up to two non-adjacent saturated carbons of the chain are optionally replaced by R* wherein R* is —C(O)—, —C(O)C(O)—, —C(O)NR—, —C(O)NRNR—, —C(O)O—, —OC(O)—, —$NRCO_2$—, —O—, —NRC(O)NR—, —OC(O)NR—, —NRNR—, —NRC(O)—, —S—, —SO—, —$SO_2$—, —NR—, —$SO_2$NR—, or —$NRSO_2$—; wherein R is selected from hydrogen or optionally substituted aliphatic, cycloalkyl, heterocycloalkyl, aryl or heteroaryl, and preferably H or optionally substituted $C_{1-4}$ aliphatic. Optional substituents on the alkylidene chain are as described above for an aliphatic group. Alternatively, the linker group is R*.

The term "treatment" refers to any treatment of a pathologic condition in a mammal, particularly a human, and includes: (i) preventing the pathologic condition from occurring in a subject which may be predisposed to the condition but has not yet been diagnosed with the condition and, accordingly, the treatment constitutes prophylactic treatment for the disease condition; (ii) inhibiting the pathologic condition, i.e., arresting its development; (iii) relieving the pathologic condition, i.e., causing regression of the pathologic condition; or (iv) relieving the conditions mediated by the pathologic condition.

The term "therapeutically effective amount" refers to that amount of a compound of the invention that is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "pharmaceutically acceptable salts" includes, but is not limited to, salts well known to those skilled in the art, for example, mono-salts (e.g. alkali metal and ammonium salts) and poly salts (e.g. di- or tri-salts,) of the compounds of the invention. Pharmaceutically acceptable salts of compounds of formulas (I), (II), (III), or (IV) are where, for example, an exchangeable group, such as hydrogen in —OH, —NH—, or —P(=O)(OH)—, is replaced with a pharmaceutically acceptable cation (e.g. a sodium, potassium, or ammonium ion) and can be conveniently be prepared from a corresponding compound of formula (I) by, for example, reaction with a suitable base. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts include quaternary ammonium salts formed with R'Y; where Y is selected from halogen, tosylate, methanesulfonate, benzenesulfonate, trifluoromethanesulfonate and the like; and R' is selected from an optionally substituted cycloalkyl, heterocycloalkyl, aryl or heteroaryl.

Suitable acids include hydrofluoric acid, hydrochloric acid, hydrobromic acid, hydriodic acid, sulfuric acid, nitric acid, phosphoric acid, carbonic acid, boric acid, selenious acid, hydrogen sulfide, phosphomolybdic acid, phosphorous acid, sulfurous acid, citric acid, maleic acid, D-malic acid, L-lactic acid, D-lactic acid, DL-lactic acid, oxalic acid, methanesulfonic acid, valeric acid, oleic acid, lauric acid, paratoluenesulfonic acid, 1-naphthalensulfonic acid, 2-naphthalensulfonic acid, phthalic acid, tartaric acid, L-malic acid, DL-malic acid, malonic acid, succinic acid, fumaric acid, glycolic acid, thioglycolic acid, glycine, sarcocine, sulfonic acid, nicotinic acid, picolinic acid, isonicotinic acid, benzoic acid and substituted benzoic acid where benzene ring bears one or more substituents.

Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The term "prodrug" or "prodrugs" is used in its ordinary meaning in the art and means a compound of the invention that has its charged moieties masked or protected by another moiety that is designed to be cleaved under particular physiological conditions, leaving the deprotected or unmasked compound of the invention. The use of masking agents is common and well-known in the art and, in particular, masking phosphate or phosphonate groups. All such masking agents are suitable and can be used with the compounds of the invention. Various agents such as acyloxy alkyl esters are described by Srivasta et al., (1984 *Bioorganic Chemistry* 12, 118-12), and by Freeman et al. (1997 *Progress in Medicinal Chemistry* 34:112-147) which are each incorporated in their entirety herein by reference; and 3-phthalidyl phosphonate esters are described by Dang Q., et al., (1999 *Bioorganic & Med. Chem. Letters*, 9:1505-1510), which is incorporated in its entirety herein by reference. For example, and not by way of limitation, Srivasta et al. also describe acetoxymethyl, isobutryloxymethyl, and pivaloxymethyl as masking agents. Other suitable masking groups comprising pivaloxyalkyl, e.g., pivaloxymethyl, or a pivaloyloxy group as described by Farquhar D. et al., (1995 *J. Med. Chem.*, 38:488-495) which is incorporated in its entirety herein by reference. Still other masking or protecting agents are described in U.S. Pat. Nos. 4,816,570 and 4,968,788 both of which are incorporated in their entirety herein by reference. Lipid prodrugs are also suitable for use with the compounds of the invention. By non-limiting example, certain lipid prodrugs are described in Hostetler et al., (1997 *Biochem. Pharm.* 53:1815-1822), and Hostetler et al., 1996 *Antiviral Research* 31:59-67), both of which are incorporated in their entirety herein by reference. Additional examples of suitable prodrug technology is described in WO 90/00555; WO 96/39831; WO 03/095665A2; U.S. Pat. Nos. 5,411,947; 5,463,092; 6,312,662; 6,716,825; and U.S. Published Patent Application Nos. 2003/0229225 and 2003/0225277 each of which is incorporated in their entirety herein by reference. Such prodrugs may also possess the ability to target the drug compound to a particular tissue within the patient, e.g., liver, as described by Erion et al., (2004 *J. Am. Chem. Soc.* 126:5154-5163; Erion et al., *Am. Soc. Pharm. & Exper. Ther. DOI*:10.1124/jept.104.75903 (2004); WO 01/18013 A1; U.S. Pat. No. 6,752,981), each of which is incorporated in their entirety herein by reference. By way of non-limiting example, other prodrugs suitable for use with the compounds of the invention are described in WO 03/090690; and by Harris et al., (2002 *Antiviral Chem & Chemo.* 12: 293-300; Knaggs et al., 2000 *Bioorganic & Med. Chem. Letters* 10: 2075-2078) each of which is incorporated in their entirety herein by reference.

The invention relates to the ability of the α-methylene-γ-butyrolactone moiety in sesquiterpene lactones to be structurally modified by, for example, Michael addition with amines or thiols. Modification of the parthenolide (1) molecule by this methodology using primary and/or secondary amines to form water-soluble amino derivatives, affords amine adducts that can easily be obtained as different inorganic or organic salts to further increase water solubility. Thus, a novel class of more water-soluble parthenolide analogs is described. When compounds in this class were evaluated for antileukemic activity, it was found that these compounds were either equipotent as, or more potent than the parent compound, parthenolide. More importantly, these novel analogs showed greater cytotoxicity towards leukemia cells than towards normal cells. Thus, the present invention provides a new class of parthenolide derivatives with potent and selective anticancer activities.

In accordance with the present invention, there are provided compounds of formula (I):

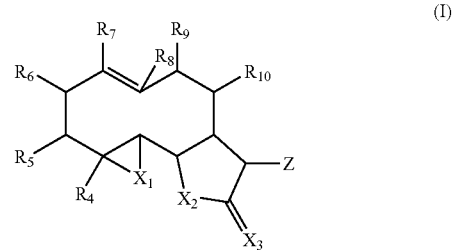

(I)

wherein:

$X_1$, $X_2$ and $X_3$ are heteroatoms;

$R_4$, $R_5$, $R_6$, $R_7$, $R_8$, $R_9$ and $R_{10}$ are independently selected from H, halo, —OH, —NO$_2$, —CN and optionally substituted aliphatic, cycloalkyl, heterocycloalkyl, aryl or heteroaryl; and Z is optionally substituted $C_{1-8}$ straight-chained or branched aliphatic, optionally containing 1 or more double or triple bonds, wherein one or more carbons are optionally replaced by R* wherein R* is optionally substituted cycloalkyl, heterocycloalkyl, aryl or heteroaryl; an amino acid residue, H, —CN, —C(O)—, —C(O)C(O)—, —C(O)NR$^1$—, —C(O)NR$^1$NR$^2$—, —C(O)O—, —OC(O)—, —NR$^1$CO$_2$—, —O—, —NR$^1$C(O)NR$^2$—, —OC(O)NR$^1$—, —NR$^1$NR$^2$—, —NR$^1$C(O)—, —S—, —SO—, —SO$_2$—, —NR$^1$—, —SO$_2$NR$^1$—, —NR$^1$R$^2$, or —NR$^1$SO$_2$—, wherein R$^1$ and R$^2$ are independently selected from H and optionally substituted aliphatic, cycloalkyl, heterocycloalkyl, aryl or heteroaryl; or where R* is NR$^1$R$^2$, R$^1$ and R$^2$ optionally together with the nitrogen atom form an optionally substituted 5-12 membered ring, said ring optionally comprising 1 or more heteroatoms and/or a group selected from —CO—, —SO—, —SO$_2$— and —PO—; or a pharmaceutically acceptable salt, ester or prodrug thereof.

Presently preferred compounds include compounds of formula (I) wherein $R_5$, $R_6$, $R_7$, $R_9$ and $R_{10}$ are independently selected from H, halo, —OH, —NO$_2$, —CN, —CH$_3$, —CF$_3$, —CH$_2$CH$_3$, —CH$_2$CF$_3$, —CH$_2$Cl, —CH$_2$OH, —CH$_2$CH$_2$OH and —CH$_2$NH$_2$. Further preferred embodiments include compounds where $R_5$, $R_6$, $R_7$, $R_9$ and $R_{10}$ are each H.

Other preferred embodiments of the present invention include compounds where $R_4$ and $R_5$ are independently selected from optionally substituted $C_1$-$C_4$ alkyl. In one preferred embodiment, $R_4$ is —$CH_3$, and in another, $R_4$ and $R_8$ are each —$CH_3$.

In one embodiment $X_1$, $X_2$ and $X_3$ are heteroatoms independently selected from O, N and S, and in one particular embodiment, $X_1$, $X_2$ and $X_3$ are each O.

According to one embodiment, it is preferred that where $R_5$, $R_6$, $R_7$, $R_9$ and $R_{10}$ are H, $R_4$ and $R_5$ are each —$CH_3$, and $X_1$, $X_2$ and $X_3$ are each O; Z is not =$CH_2$.

According to a further embodiment of the invention, Z is —$(CH_2)_m$—$NR^1R^2$ where m is an integer from 0 to 4, where preferably, $R_5$, $R_6$, $R_7$, $R_9$, and $R_{10}$ are H; and $R_4$ and $R_5$ are each —$CH_3$. In one particular embodiment, m is 1. In other embodiments, $R^1$ and $R^2$ are independently selected from hydrogen, —CN or optionally substituted $C_1$-$C_4$ alkyl. In particular embodiments, $R^1$ and $R^2$ are independently selected from —$NO_2$, —CN, —$CH_3$, —$CF_3$, —$CH_2CH_3$, —$CH_2CF_3$, —$CH_2Cl$, —$CH_2OH$, —$CH_2CH_2OH$ and —$CH_2NH_2$.

In yet a further embodiment, $R^1$ and $R^2$ together with N form an optionally substituted ring. The ring is a monocyclic, bicyclic or tricyclic aliphatic or aryl ring system, where the ring system is optionally substituted and optionally comprises one or more heteroatoms or a group selected from —CO—, —SO—, —$SO_2$— and —PO—. In one particular embodiment, $R^1$ and $R^2$ are —$CH_2(CH_2)_nCH_2Y$—, where Y is a heteroatom or a group selected from —CO—, —SO—, —$SO_2$— and —PO—; n is an integer 0 to 5; and together with N form an optionally substituted ring, which may be additionally fused to a cycloalkyl or aryl group to form a bicyclic or tricyclic ring system, where the system is optionally substituted and optionally comprises one or more heteroatoms. Alternatively, $R_1$ and $R_2$ are —$(CH_2)_a$—Y—$(CH_2)_b$—, where Y is a heteroatom or a group selected from —CO—, —SO—, —$SO_2$— and —PO—; a is an integer 0 to 5; b is an integer 0 to 5; where the sum of a and b is 0 to 5; and together with N form an optionally substituted ring, the ring being optionally fused to a cycloalkyl or aryl group to form a bicyclic or tricyclic ring system, where the system is optionally substituted and optionally compries one or more heteroatoms.

Examples of ring systems include an optionally substituted uracil ring or a derivative thereof. Other examples include optionally substitute pyrrole, imidazole, purine and pyrazole and derivative thereof. Examples of fused ring systems include optionally substituted aziridin-1-yl, azetidin-1-yl, pyrrolidin-1-yl, piperidin-1-yl, homopiperidyn-1-yl and heptamethyleneimin-1-yl.

According to a further embodiment of the invention, Z is —$(CH_2)_m$—$S(O)_n$—$R^1$ where m is an integer from 0 to 4, n is an integer from 0 to 2, where preferably, $R_5$, $R_6$, $R_7$, $R_9$, and $R_{10}$ are H; and $R_4$ and $R_5$ are each —$CH_3$. In one particular embodiment, m is 1.

In another embodiment n is 0. In other embodiments, $R^1$ is independently selected from hydrogen, —CN, optionally substituted $C_1$-$C_4$ alkyl or aryl. In particular embodiments, $R^1$ is selected from —$C_6H_5$, —$CH_2CH(CO_2H)(NH_2)$, and —$CH_2CO_2H$.

Exemplary compounds of the present invention include:
11S,11,13-Dihydro,13-dimethylaminoparthenolide (DMAPT);
11S,11,13-Dihydro,13-diethylaminoparthenolide;
11S,11,13-Dihydro,13-(tert-butylamino)parthenolide;
11S,11,13-Dihydro,13-(pyrrolidin-1-yl)parthenolide;
11S,11,13-Dihydro,13-(piperidin-1-yl)parthenolide (PIPT);
11S,11,13-Dihydro,13-(morpholin-1-yl)parthenolide;
11S,11,13-Dihydro,13-(4-methylpiperidin-1-yl)parthenolide (4MEPT);
11S,11,13-Dihydro,13-(4-methylpiperazin-1-yl)parthenolide;
11S,11,13-Dihydro,13-(homopiperidin-1-yl)parthenolide;
11S,11,13-Dihydro,13-(heptamethyleneimin-1-yl)parthenolide;
11S,11,13-Dihydro,13-(azetidin-1-yl)parthenolide;
11S,11,13-Dihydro,13-methylbutylaminoparthenolide;
11S,11,13-Dihydro,13-methyl pentylaminoparthenolide;
11S,11,13-Dihydro,13-ethylaminoparthenolide;
11S,11,13-Dihydro,13-methylaminoparthenolide;
11S,11,13-Dihydro,13-cyclopropylaminoparthenolide;
11S,11,13-Dihydro,13-propargylaminoparthenolide;
11S,11,13-Dihydro,13-(N-benzyl-N-ethylamine)parthenolide;
11S,11,13-Dihydro,13-(N-prolyl)parthenolide;
11S,11,13-Dihydro,13-(S-thiophenolyl)parthenolide;
11S,11,13-Dihydro,13-(N,N-diethanolamine)parthenolide
11S,11,13-Dihydro,13-(thiomorpholin-4-yl)parthenolide;
11S,11,13-Dihydro,13-(4-hydroxypiperidin-1-yl)parthenolide;
11S,11,13-Dihydro,13-(1-methylhomopiperizin-4-yl)parthenolide;
11S,11,13-Dihydro,13-(S-mercaptoacetyl)parthenolide;
11S,11,13-Dihydro,13-(4-(2'-hydroxyethyl)piperidin-1-yl)parthenolide;
11S,11,13-Dihydro,13-(piperazin-1-yl-4-carboxaldehyde)parthenolide;
11S,11,13-Dihydro,13-(4-benzylpiperidin-1-yl)parthenolide;
11S,11,13-Dihydro,13-(piperidin-1-yl-4-carboxylic acid)parthenolide;
11S,11,13-Dihydro,13-(azetidin-1-yl-3-carboxylic acid)parthenolide;
11S,11,13-Dihydro,13-(S-cysteinyl)parthenolide;
11S,11,13-Dihydro,13-(4-(piperidin-1'-yl)piperidin-1-yl))parthenolide; and
11S,11,13-Dihydro,13-diallylaminoparthenolide.

Those of skill in the art will recognize that the invention comprises compounds that may contain one or more chiral centers on, for example, the parthenolide C-11 and thus can exist as racemic mixtures as pure diastereomers, or as pure enantiomers. For many applications, it is preferred to carry out stereoselective synthesis and/or to subject the reaction product to appropriate purification steps so as to produce substantially stereochemically pure or optically pure materials. Suitable stereoselective synthetic procedures for producing stereochemically pure or optically pure materials are well known in the art, as are procedures for resolving racemic mixtures into their optically pure enantiomers.

The present invention further provides for compounds having formula (I), or a pharmaceutically acceptable salt thereof, wherein Z is a group that is converted to =$CH_2$ under physiological conditions during or after administration to a mammalian patient, thereby yielding a methylene group. In particular embodiments $X_1$, $X_2$ and $X_3$ are 0; $R_5$, $R_6$, $R_7$, $R_9$, and $R_{10}$ are H; $R_4$ and $R_5$ are —$CH_3$; and Z is optionally substituted $C_{1-8}$ straight-chained or branched aliphatic, optionally containing 1 or more double or triple bonds, wherein one or more carbons are optionally replaced by R* wherein R* is optionally substituted cycloalkyl, heterocycloalkyl, aryl or heteroaryl; an amino acid residue, H, —CN, —C(O)—, —C(O)C(O)—, —C(O)$NR^1$—, —C(O)$NR^1NR^2$—, —C(O)O—, —OC(O)—, —$NR^1CO_2$—, —O—, —$NR^1C(O)NR^2$—, —OC(O)$NR^1$—, —$NR^1NR^2$—, —$NR^1C(O)$—, —S—, —SO—, —$SO_2$—, —$NR^1$—, —$SO_2NR^1$—, —$NR^1R^2$, or —$NR^1SO_2$—, wherein $R^1$ and $R^2$ are independently selected from H and optionally substituted aliphatic, cycloalkyl, heterocycloalkyl, aryl or heteroaryl. In preferred embodiments Z is —$CH_2N(CH_3)_2$, —$CH_2N(H)(C(CH_3)_3)$, —$CH_2N(CH_2CH_3)_2$, —$CH_2N(CH_2CH=CH_2)_2$, —$CH_2$-azetidine, —$CH_2$-pyrrolidine, —$CH_2$-piperidine, —$CH_2$-homopiperidine, —$CH_2$-heptamethyleneimine, —$CH_2$-4-methylpiperidine, —$CH_2$-morpholine, —$CH_2$-pyrrolidine, —$CH_2$-proline, —$CH_2$-thiophenol, —$CH_2$-diethanolamine, —CH$_2$-hydroxypiperidine, —CH$_2$-methylhomopiperazine, —CH$_2$-thiomorpholine, —CH$_2$-mercaptoacetic acid, —CH$_2$-benzylpiperidine, —CH$_2$-piperidine-4-carboxylic acid, —CH$_2$-azetidine-3-carboxylic acid, —CH$_2$-piperidinylpiperidine, or —CH$_2$-cysteine.

The present invention further provides for compounds having formula (I), or a pharmaceutically acceptable salt thereof, wherein Z is CH$_2$N(CH$_3$)$_2$ which under physiological conditions during or after administration to a mammalian patient, undergoes mono- or di-demethylation; conversion to =CH$_2$, or cysteine or protein conjugation. In particular embodiments, $X_1$, $X_2$ and $X_3$ are O; $R_5$, $R_6$, $R_7$, $R_9$, and $R_{10}$ are H; $R_4$ and $R_8$ are —CH$_3$;

The present invention further provides compounds wherein the parthenolide based derivatives of formula (I) form dimers or duplexes with another molecule of formula (I) or with basic nitrogen-containing synergistic anticancer drug molecules such as 5-fluorouracil, cytarabine, mytomycin C, Doxorubicin and Daunorubicin. Accordingly, the present invention provides compounds of the general formula (II):

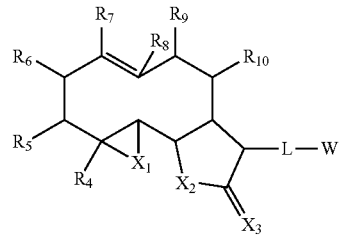

(II)

where L is a linker, as defined above, and W is a molecule with anti-cancer growth activity. Where W is another parthenolide derivative of formula (I), the present invention provides compounds of formula (III):

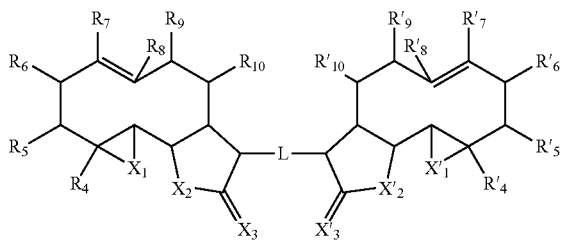

(III)

where $R'_4$, $R'_5$, $R'_6$, $R'_7$, $R'_8$, $R'_9$, $R'_{10}$, $X'_1$, $X'_2$ and $X'_3$ are independently as defined above for their counterparts, $R_6$, $R_7$, $R_8$, $R_9$, $R_{10}$, $X_1$, $X_2$ and $X_3$; and L is a linker, as defined above. Preferred linkers include optionally substituted alkyl and amine groups. In one particular embodiment, L is —CH$_2$N(R)CH$_2$—, where R is as defined above. Included are pharmaceutically acceptable salts formed with inorganic and/or organic acids, as defined above for compounds of formula (I).

In accordance with another embodiment of the invention, the methods for the preparation of the amino analogs described in this invention are disclosed in Schemes I and II.

Scheme I

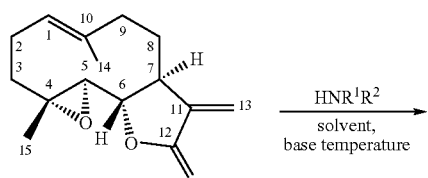

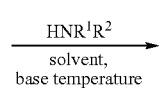

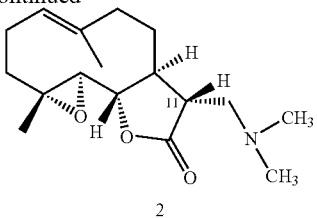

Scheme II

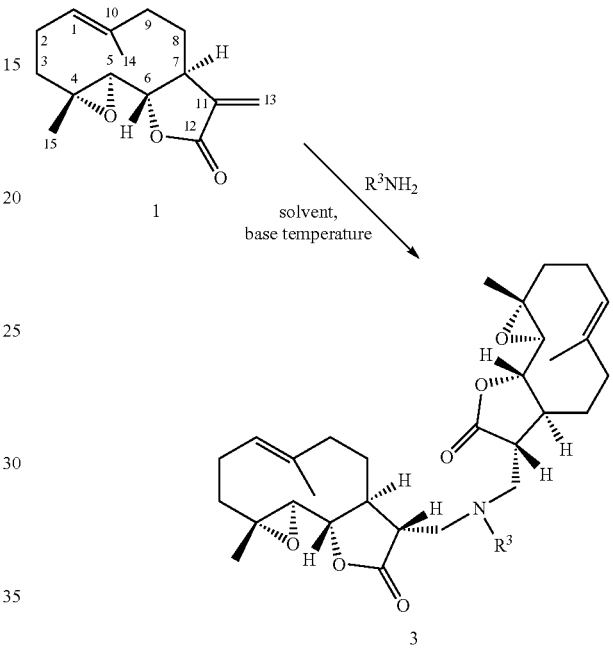

In the above scheme, the solvent is selected from a low alkyl alcohol, such as methanol, ethanol, propanol, isopropanol, n-butanol, tert-butanol, and chloroform, methylene chloride, benzene, toluene, tetrahydrofuran, dioxane, 1,2-dimethoxyethane, pyridine, carbon tetrachloride, diethyl ether, tert-butyl methyl ether and/or the mixture of two or more of the solvents listed above. The base is selected from a low trialkylamine, such as trimethylamine, triethylamine, tripropylamine, and tributylamine, and pyridine, 2-, 3-, and 4-picolines, 2-, 3-, and 4-dimethylaminopyridines. The temperature is selected from −20° C. to 130° C. The reaction time required to effect the desired coupling reaction can vary widely, typically falling in the range of 30 min to 24 hours. Purification can be achieved by a variety of techniques, such as, liquid chromatography through neutral or basic silica gel, bonded silica gel phases such as octadecylsilica, octylsilica and the like, cellulose or alumina with the solvent such as, for example, the mixture of chloroform and methanol or ethanol, the mixture of methylene chloride and methanol or ethanol, the mixture of hexane and acetone or acetonitrile or methanol or ethanol or isopropanol, the mixture of diethyl ether and acetone or acetonitrile or methanol or ethanol or isopropanol; and recrystallization using normal organic solvent or solvent mixture, such as methanol, ethanol, propanol, isopropanol, tert-butanol, acetonitrile, diethyl ether, chloroform, methylene chloride and the mixture of two or more solvents listed above. The purity of the invention compounds prepared is assessed by mass spectrometry, nuclear magnetic resonance spectrometry (NMR) and elemental combustion analysis.

Furthermore, in accordance with still another embodiment of the present invention, the methods for the preparation of the invention salts are disclosed in Schemes III and IV.

Scheme III

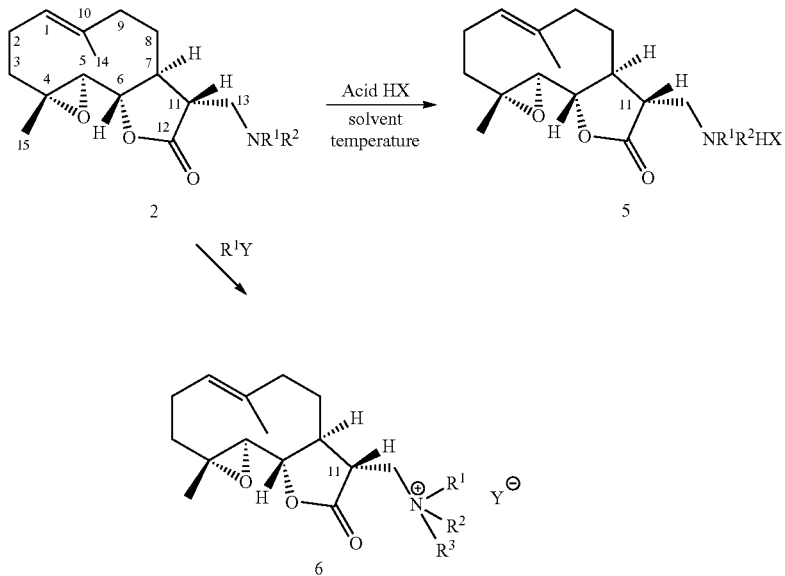

In these schemes, HX is selected from hydrochloride, hydrobromide, hydroiodide, perchlorate, sulfate, hemisulfate, mesylate, toluenesulfonate, benzenesulfonate, succinate, hemisuccinate, fumarate, tartarate, ascorbate, acetate, hemifumarate, maleate, citrate, oxalate, malonate, malic, propionate and benzoate; $Y^{\ominus}$ is selected from halide (fluoride, chloride, bromide, iodide), methylsulfonate, toluenesulfonate, benzenesulfonate and sulfate; and the solvent is selected from a low alkyl alcohol, such as diethyl ether, methanol, ethanol, propanol, isopropanol, n-butanol, tert-butanol, and chloroform, methylene chloride, benzene, toluene, tetrahydrofuran, dioxane, 1,2-dimethoxyethane, pyridine, carbon tetrachloride, tert-butyl methyl ether, acetone and/or the mixture of two or more of the solvents listed above. The temperature is selected from −20° C. to 50° C. Purification can be achieved by recrystallization using normal organic solvent or solvent mixture, such as methanol, ethanol, acetone, propanol, isopropanol, t-butanol, acetonitrile, diethyl ether, chloroform, methylene chloride and the mixture of two or more solvents listed above.

Scheme IV

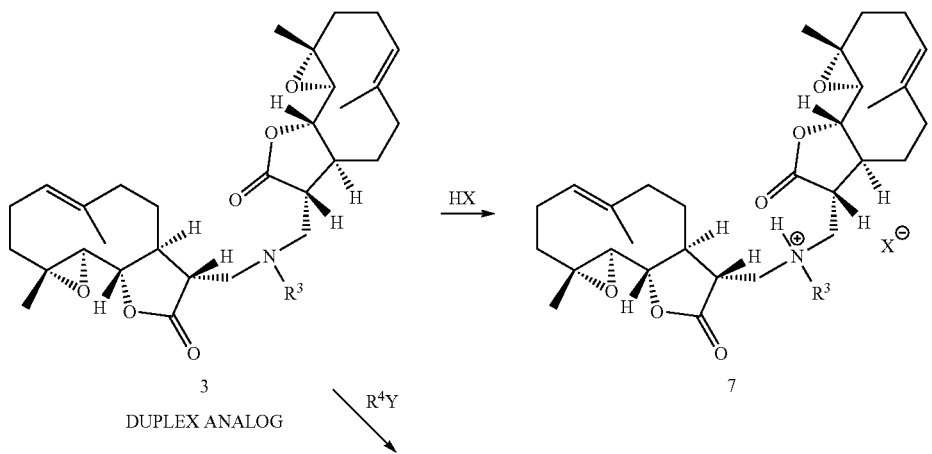

DUPLEX ANALOG

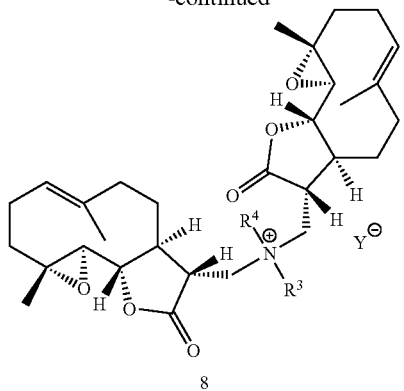

8

The present invention further provides analogues of compounds of formula (I). Examples are described below and include costunolide, dehydrocostuslactone, alantolactone, isoalantolactone, amino-3-oxo-isoalantolactone, helenalin, 11,13-dihydrohelenalin, aminocyanaropicrin, aminodesacylcyanaropicrin, (+)-aminoreyonosin, aminosantamarin, aminosoulangianolide and aminoisotelekin. In addition, the present invention provides compounds of the analogues below, amino-3-oxo-isoalantolactone, aminocyanaropicrin, aminodesacylcyanaropicrin, (+)-aminoreyonosin, aminosantamarin, aminosoulangianolide and aminoisotelekin wherein (—CH$_2$—NR$_1$R$_2$) is replaced by Z, where Z is as defined herein.

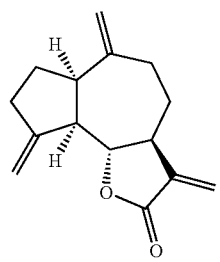

Dehydrocostuslactone

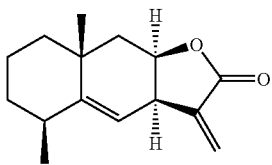

Alantolactone

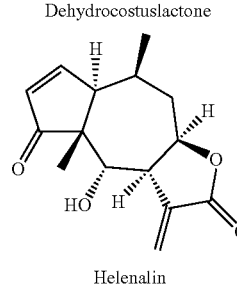

Helenalin

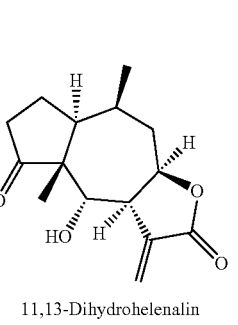

Isoalantolactone

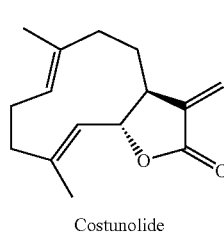

Costunolide

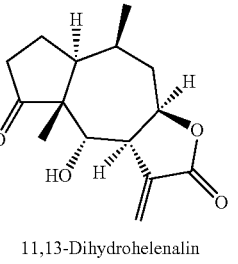

11,13-Dihydrohelenalin

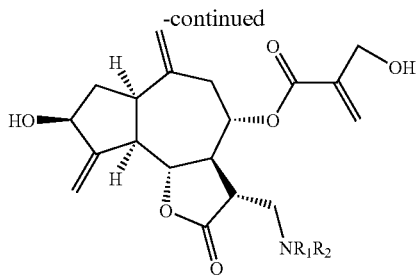

Aminocynaropicrins

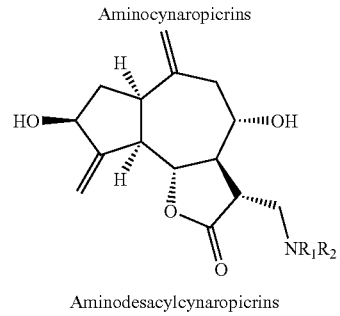

Aminodesacylcynaropicrins

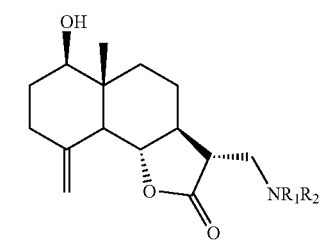

(+)-Aminoreynosins

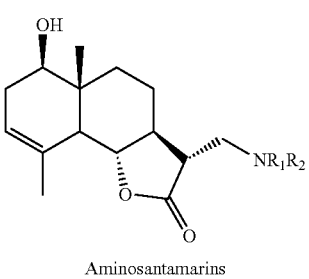

Aminosantamarins

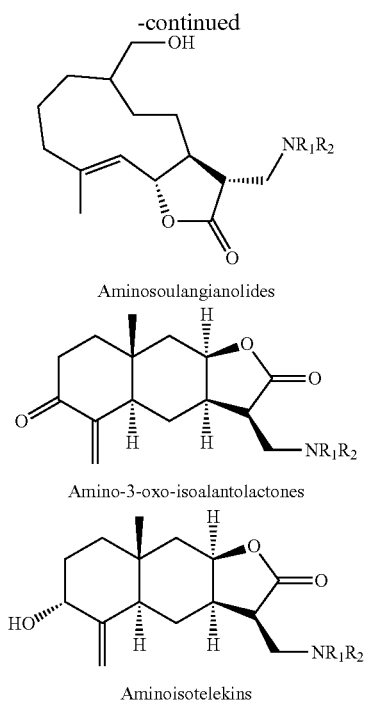

Aminosoulangianolides

Amino-3-oxo-isoalantolactones

Aminoisotelekins

The invention relates to the ability of the α-methylene-γ-butyrolactone moiety in all the above-mentioned sesquiterpene lactones to be structurally modified by, for example, Michael addition with the following chemical entities to form more water-soluble derivatives than the corresponding parent sesquiterpene, and with improved properties conducive for drug development, such as, chemical stability, reduced toxicity and oral bioavailability.

The present invention further provides compounds of the parthenolide-analog dehydrocostuslactone based derivatives of formula (IV):

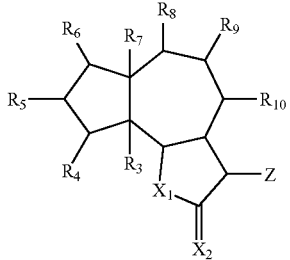

(IV)

Presently preferred compounds include compounds of formula (IV) wherein $R_3$, $R_5$, $R_6$, $R_9$ and $R_{10}$ are independently selected from H, halo, —OH, —$NO_2$, —CN, —$CH_3$, —$CF_3$, —$CH_2CH_3$, —$CH_2CF_3$, —$CH_2Cl$, —$CH_2OH$, —$CH_2CH_2OH$ and —$CH_2NH_2$. Further preferred embodiments include compounds where $R_3$, $R_5$, $R_6$, $R_9$ and $R_{10}$ are each H.

Other preferred embodiments of the present invention include compounds where $R_4$ and $R_8$ are independently selected from optionally substituted $C_1$-$C_4$ alkyl. In one preferred embodiment, $R_4$ and $R_8$ are each =$CH_2$.

In one embodiment $X_1$ and $X_2$ are heteroatoms independently selected from O, N and S, and in one particular embodiment, $X_1$ and $X_2$ are each O.

According to a further embodiment of the invention, Z is —$(CH_2)_m$—$NR^1R^2$ where m is an integer from 0 to 4, where preferably, $R_5$, $R_6$, $R_7$, $R_9$ and $R_{10}$ are H; and $R_4$ and $R_8$ are each —$CH_3$. In one particular embodiment, m is 1. In other embodiments, $R^1$ and $R^2$ are independently selected from hydrogen, —CN or optionally substituted $C_1$-$C_4$ alkyl. In particular embodiments, $R^1$ and $R^2$ are independently selected from —$NO_2$, —CN, —$CH_3$, —$CF_3$, —$CH_2CH_3$, —$CH_2CF_3$, —$CH_2Cl$, —$CH_2OH$, —$CH_2CH_2OH$ and —$CH_2NH_2$.

In yet a further embodiment, $R^1$ and $R^2$ together with N form an optionally substituted ring. The ring is a monocyclic, bicyclic or tricyclic aliphatic or aryl ring system, where the ring system is optionally substituted and optionally comprises one or more heteroatoms or a group selected from —CO—, —SO—, —$SO_2$— and —PO—. In one particular embodiment, $R^1$ and $R^2$ are —$CH_2$ $(CH_2)_n CH_2Y$—, where Y is a heteroatom or a group selected from —CO—, —SO—, —$SO_2$— and —PO—; n is an integer 0 to 5; and together with N form an optionally substituted ring, which may be additionally fused to a cycloalkyl or aryl group to form a bicyclic or tricyclic ring system, where the system is optionally substituted and optionally comprises one or more heteroatoms. Alternatively, $R_1$ and $R_2$ are —$(CH_2)_a$—Y—$(CH_2)_b$—, where Y is a heteroatom or a group selected from —CO—, —SO—, —$SO_2$— and —PO—; a is an integer 0 to 5; b is an integer 0 to 5; where the sum of a and b is 0 to 5; and together with N form an optionally substituted ring, the ring being optionally fused to a cycloalkyl or aryl group to form a bicyclic or tricyclic ring system, where the system is optionally substituted and optionally compries one or more heteroatoms.

Examples of ring systems include an optionally substituted uracil ring or a derivative thereof. Other examples include optionally substitute pyrrole, imidazole, purine and pyrazole and derivative thereof. Examples of fused ring systems include optionally substituted aziridin-1-yl, azetidin-1-yl, pyrrolidin-1-yl, piperidin-1-yl, homopiperidyn-1-yl and heptamethyleneimin-1-yl.

With respect to formulas (I) and (IV), in other embodiments, Z is hydroxylamine, a hydroxyalkylamino compound, a thioalkylamino compound, a diaminoalkane. Examples include ethylenediamine, piperazine, triaminoalkanes, polyamines, polylysine, putrescine, spermine, spermidine, aminoguanidines and agmatine. In other embodiments, Z is an amino acid. For example glycine, serine, hydroxyproline, β-alanine, cysteine, homocysteine, arginine, lysine, glutamic acid, ornithine, aspartic acid, γ-aminobutyric acid, or taurine. In other embodiments, Z is an amino sugar; for example glucosamine. In other embodiments, Z is a polyoxyethylene glycol of various molecular weights, each of which terminate in an amino functionality that will form an adduct with the appropriate sesquiterpene.

Modification of the sesquiterpene molecules by these methodologies, affords adducts that can easily be obtained as different inorganic or organic salts to further increase water solubility.

The compounds described herein are useful for treating cancer. Cancers treatable by the present therapy include the solid and hematological tumors, such as prostate cancer, ovarian cancer, breast cancer, brain cancer and hepatic cancer, comprising administering to a mammal afflicted with said cancer an amount of parthenolide derivative effective to inhibit the viability of cancer cells of said mammal. The parthenolide derivative may be administered as primary therapy, or as adjunct therapy, either following local intervention (surgery, radiation, local chemotherapy) or in conjunction with at least one other chemotherapeutic agent discussed hereinabove, as well as the solid tumors disclosed in U.S. Pat. No. 5,514,555. Hematological cancers, such as the leukemias are disclosed in the Mayo Clinic Family Health Book, D. E. Larson, ed., William Morrow, N.Y. (1990) and include CLL, ALL, CML and the like. Compounds of the present invention may be used in bone marrow transplant procedure to treat bone marrow prior to reintroduction to the patient. In addition, the compounds of the present invention may be used as chemotherapy sensitizers or radiation therapy sensitizers. Accordingly, a patient, or cells, or tissues, derived from a cancer patient, are pre-treated with the compounds prior to standard chemotherapy or radiation therapy. The present invention contemplates that parthenolide may also be used in such methods.

Within another aspect of the present invention, methods are provided for inhibiting angiogenesis in patients with non-tumorigenic, angiogenesis-dependent diseases, comprising administering a therapeutically effective amount of a composition comprising parthenolide derivative to a patient with a non-tumorigenic angiogenesis-dependent disease, such that the formation of new blood vessels is inhibited. Within other aspects, methods are provided for inhibit reactive proliferation of endothelial cells or capillary formation in non-tumorigenic, angiogenesis-dependent diseases, such that the blood vessel is effectively occluded. Within one embodiment, the anti-angiogenic composition comprising parthenolide derivative is delivered to a blood vessel which is actively proliferating and nourishing a tumor.

In addition to tumors, numerous other non-tumorigenic angiogenesis-dependent diseases, which are characterized by the abnormal growth of blood vessels, may also be treated with the anti-angiogenic parthenolide derivative compositions, or anti-angiogenic factors of the present invention. Anti-angiogenic parthenolide derivative compositions of the present invention can block the stimulatory effects of angiogenesis promoters, reducing endothelial cell division, decreasing endothelial cell migration, and impairing the activity of the proteolytic enzymes secreted by the endothelium. Representative examples of such non-tumorigenic angiogenesis-dependent diseases include corneal neovascularization, hypertrophic scars and keloids, proliferative diabetic retinopathy, arteriovenous malformations, atherosclerotic plaques, delayed wound healing, hemophilic joints, nonunion fractures, Osler-Weber syndrome, psoriasis, pyogenic granuloma, scleroderma, trachoma, menorrhagia, retrolental fibroplasia and vascular adhesions. The pathology and treatment of these conditions is disclosed in detail in published PCT application PCT/CA94/00373 (WO 95/03036), at pages 26-36. Topical or directed local administration of the present compositions is often the preferred mode of administration of therapeutically effective amounts of parthenolide derivative, i.e., in depot or other controlled release forms.

Anti-angiogenic compositions of the present invention may also be utilized in a variety of other manners. For example, they may be incorporated into surgical sutures in order to prevent stitch granulomas, implanted in the uterus (in the same manner as an IUD) for the treatment of menorrhagia or as a form of female birth control, administered as either a peritoneal lavage fluid or for peritoneal implantation in the treatment of endometriosis, attached to a monoclonal antibody directed against activated endothelial cells as a form of systemic chemotherapy, or utilized in diagnostic imaging when attached to a radioactively labelled monoclonal antibody which recognizes active endothelial cells. The magnitude of a prophylactic or therapeutic dose of parthenolide derivative, an analog thereof or a combination thereof, in the acute or chronic management of cancer, i.e., prostate or breast cancer, will vary with the stage of the cancer, such as the solid tumor to be treated, the chemotherapeutic agent(s) or other anti-cancer therapy used, and the route of administration. The dose, and perhaps the dose frequency, will also vary according to the age, body weight, and response of the individual patient. In general, the total daily dose range for parthenolide derivative and its analogs, for the conditions described herein, is from about 0.5 mg to about 2500 mg, in single or divided doses. Preferably, a daily dose range should be about 1 mg to about 100 mg, in single or divided doses, most preferably about 5-50 mg per day. In managing the patient, the therapy should be initiated at a lower dose and increased depending on the patient's global response. It is further recommended that infants, children, patients over 65 years, and those with impaired renal or hepatic function initially receive lower doses, and that they be titrated based on global response and blood level. It may be necessary to use dosages outside these ranges in some cases. Further, it is noted that the clinician or treating physician will know how and when to interrupt, adjust or terminate therapy in conjunction with individual patient response. The terms "an effective amount" or "an effective sensitizing amount" are encompassed by the above-described dosage amounts and dose frequency schedule.

Any suitable route of administration may be employed for providing the patient with an effective dosage of parthenolide derivative (e.g., oral, sublingual, rectal, intravenous, epidural, intrethecal, subcutaneous, transcutaneous, intramuscular, intraperitoneal, intracutaneous, inhalation, transdermal, nasal spray, nasal gel or drop, and the like). While it is possible that, for use in therapy, parthenolide derivative or its analogs may be administered as the pure chemicals, as by inhalation of a fine powder via an insufflator, it is preferable to present the active ingredient as a pharmaceutical formulation. The invention thus further provides a pharmaceutical formulation comprising parthenolide derivative or an analog thereof, together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof, such as a human patient or domestic animal.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The formulations may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

Pharmaceutical formulations suitable for oral administration may be presented as discrete unit dosage forms such as hard or soft gelatin capsules, cachets or tablets each containing a predetermined amount of the active ingredient; as a powder or as granules; as a solution, a suspension or as an emulsion; or in a chewable base such as a synthetic resin or chicle for ingestion of the agent from a chewing gum. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g., by injection, for example, bolus injection or continuous infusion) and may be presented in unit dose form in ampules, pre-filled syringes, small volume infusion containers or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in A. Fisher et al. (U.S. Pat. No. 4,788,603), or R. Bawa et al. (U.S. Pat. Nos. 4,931,279; 4,668,506 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described formulations can be adapted to give sustained release of the active ingredient employed, e.g., by combination with certain hydrophilic polymer matrices, e.g., comprising natural gels, synthetic polymer gels or mixtures thereof. The polymer matrix can be coated onto, or used to form, a medical prosthesis, such as a stent, valve, shunt, graft, or the like.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing, in addition to the active ingredient, such carriers as are known in the art to be appropriate.

For administration by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the compounds of the invention may be administered via a liquid spray, such as via a plastic bottle atomizer. Typical of these are the Mistometer® (Wintrop) and the Medihaler® (Riker).

For topical administration to the eye, the compounds can be administered as drops, gels (U.S. Pat. No. 4,255,415), gums (see U.S. Pat. No. 4,136,177) or via a prolonged-release ocular insert.

The invention will now be described in greater detail by reference to the following non-limiting examples.

EXAMPLES

Example 1

General Synthetic Procedure for the Preparation of 11S,11,13-Dihydro,13-Substituted Aminoparthenolides A mixture of parthenolide (Sigma P 0667, 100 mg, 0.4 mmol), the appropriate primary amine or secondary amine (2 mmol), and triethylamine (1 to 2 mL) in 30 mL of anhydrous ethanol was stirred at a specific temperature ranging from ambient temperature to the temperature of the refluxing solvent utilized, or was left to stand in the refrigerator (−20° C. to 4° C.) overnight for 24 hours. Ethanol, triethylamine and/or the appropriate volatile amine were then evaporated under vacuum in a rotary evaporator. The resulting residue was subjected to silica gel column chromatographic purification using chloroform-methanol or methylene chloride-methanol mixed solvent as the mobile phase. NMR (Varian, 300 MHz and 400 MHz) and GC/MS (Agilent, 6890GC and 5973MSD) analysis methodologies were utilized to assure the identity and purity of the synthetic compounds.

Example 2

11S,11,13-Dihydro,13-dimethylaminoparthenolide (DMAPT)

Parthenolide (100 mg, 0.4 mmol), dimethylamine (2 M in methanol, 1 mL), triethylamine (2 mL), ethanol (30 mL) were refluxed overnight. After column purification, 109 mg of pale yellow 11S,11,13-dihydro,13-dimethylaminoparthenolide was obtained (Yield: 93%). Melting point: 143-144° C. $^1$H-NMR (300 MHz, CDCl$_3$): δ 5.22 (1H, d), 3.85 (1H, t), 2.75 (2H, m), 2.65 (1H, dd), 2.5-2.3 (3H, m), 2.25 (6H, s), 2.5-2.0 (5H, m), 1.7 (3H, s), 1.3 (3H, s), 1.3-1.15 (1H, m). $^{13}$C-NMR (300 MHz, CDCl$_3$): δ 176.1, 134.4, 124.8, 81.9, 66.4, 61.3, 57.6, 47.8, 46.4, 46.1, 41.0, 36.6, 29.9, 24.0, 17.2, 16.9. Mass Spec (GC-MS): 293 (M$^+$) Retention time: 12.56 minutes. Ultra-violet (Methanol): $\lambda_{max}$ at 214 nm. Infra-Red (Nujol): 1757.9, 1460, 1377 cm$^{-1}$. X-ray crystallographic analysis using a Nonius KappaCCD diffractometer DMAPT (11S,11,13-dihydro,13-dimethylaminoparthenolide) has the S-configuration at C-11.

Example 3

11S,11,13-Dihydro,13-diethylaminoparthenolide

Parthenolide (100 mg, 0.4 mmol), diethylamine (200 mg, 2.7 mmol), triethylamine (2 mL), ethanol (30 mL) were refluxed overnight. After column purification, 114 mg of yellow 11S,11,13-dihydro,13-diethylaminoparthenolide was obtained (Yield: 88%).

Example 4

Preparation of Salts of 11S,11,13-Dihydro,13-aminoparthenolide Derivatives

The aminoparthenolide derivative was dissolved in anhydrous ether and to this solution was added the corresponding acid in ether or ethanol. The mixture was kept in the refrigerator (4° C.) overnight. The crystals formed was filtered and dried under vacuum, or submitted to further recrystallization, if needed.

Example 5

Preparation of 11S,11,13-dihydro,13-(piperidin-1-yl)parthenolide hydrochloride 11S,11,13-dihydro,13-(piperidin-1-yl)parthenolide (5 mg) was dissolved in 2 mL of dry ether. Hydrochloride in ether (1M, 0.015 mL) was added to the ether solution until the solution became cloudy; then more ether was added and the mixture was heated to obtain a clear solution. The mixture was left in refrigerator (4° C.) for more than 24 hours. The white crystals that formed were filtered through filter paper, and dried under vacuum overnight (Yield: 18%).

Example 6

Preparation of 11S,11,13-dihydro,13-dimethylaminoparthenolide maleate

To 11S,11,13-dihydro,13-dimethylaminoparthenolide (30 mg, 0.1 mmol) in anhydrous ethanol (5 mL) was added maleic acid (12 mg, 0.1 mmol) in 3 mL of anhydrous ethanol. The solution was shaken well and filtered through a regular filter paper. The clear solution was left in the refrigerator for a week. The white crystals formed were obtained by filtration, dried in a desiccator under vacuum with anhydrous $CaCl_2$ (Yield: 55%).

Example 7

Preparation of 11S,11,13-dihydro,13-Dimethylaminoparthenolide methiodide

To 11S,11,13-dihydro,13-dimethylaminoparthenolide (30 mg, 0.1 mmol) in anhydrous methanol (5 mL) was added iodomethane (90 mg, 0.6 mmol) in methanol (1 mL). The clear solution was shaken and stored at room temperature. After three days, the methanol was evaporated, the pale yellow residue was dried in a desiccator under vacuum, over anhydrous $CaCl_2$. Recrystallization from acetone-ether afforded pale yellow crystals (Yield: 86%).

Example 8

11S,11,13-dihydro,13-(4-Methylpiperidin-1-yl)parthenolide methiodide:

To 11S,11,13-dihydro,13-(4-methylpiperidin-1-yl)parthenolide (35 mg, 0.1 mmol) in anhydrous methanol (5 mL) was added iodomethane (90 mg, 0.6 mmol) in methanol (1 mLl). The clear solution was shaken and stored at room temperature. After three days, the methanol was evaporated, the pale yellow residue was dried in a desiccator under vacuum, over anhydrous $CaCl_2$. Recrystallization from acetone-ether afforded pale yellow crystals (Yield: 79%).

Example 9

Assay for Antileukemic Activity

For apoptosis analysis, one million primary acute myelogenous leukemia (AML) cells were washed with cold PBS and resuspended in 200 microliters of Annexin binding buffer (10 mM HEPES/NaOH pH 7.4; 140 mM NaCl; 2.5 mM $CaCl_2$). Annexin V-FITC (Pharmingen) and 0.25 mg/mL 7-AAD (7-aminoactinomycin D, Molecular Probes, Calif.) were added and the tubes were incubated at room temperature in the dark for minutes. Cells were then diluted with 200 microliters of Annexin binding buffer and analyzed immediately by flow cytometry. Viable cells were identified as failing to label with Annexin V or 7-AAD. Cells beginning to die label with Annexin V, and as membrane integrity is lost, will also label with 7-AAD. For each parthenolide derivative, the percentage of viable cells was determined after 24 hours of culture at a 10 micromolar concentration. Data are normalized to untreated control specimens. The data are in Table 1 for aminoparthenolide derivatives and Table 2 for the salts of some aminoparthenolides.

Healthy human bone marrow cells were used in the above assay to test the cytotoxicity of parthenolide. Eighty-five percent of the normal cells survived 10 μM of parthenolide. All the aminoparthenolides evaluated afforded results similar to parthenolide, i.e. the survival rate of healthy human bone marrow cells was over 85% at a concentration of 10 μM.

TABLE 1

Aminoparthenolides and their antileukemic activity

| Compound | Reactants and Solvent | Reaction Conditions | Yield (%) | Antileukemic activity |
|---|---|---|---|---|
| Parthenolide | Sigma P0667 | Not applicable (N.A.) | N.A. | 10 μM, 84% |
| 11S,11,13-Dihydro, 13-dimethylaminoparthenolide | Parthenolide (100 mg), dimethylamine (2M | Refluxing overnight | 93 | 5 μM, 31% 10 μM, 90% |

TABLE 1-continued

Aminoparthenolides and their antileukemic activity

| Compound | Reactants and Solvent | Reaction Conditions | Yield (%) | Antileukemic activity |
|---|---|---|---|---|
| (DMAPT) | in methanol, 1 mL), triethylamine(2 mL), ethanol (30 mL) | | | 20 μM, 95% |
| 11S,11,13-Dihydro, 13-diethylaminoparthenolide (DEAPT) | Parthenolide (100 mg), diethylamine (200 mg, 2.7 mmol), triethylamine (2 mL), ethanol (30 mL) | Refluxing overnight | 88 | 10 μM, 60% |
| 11S,11,13-Dihydro,13-(tert-butylamino) parthenolide (tBAPT) | Parthenolide (20 mg), tert-butylamine (0.2 mL), triethylamine (0.4 mL), ethanol (5 mL) | Refluxing 10 hours | 39 | 10 μM, 20% |
| 11S,11,13-Dihydro, 13-(pyrrolidin-1-yl) parthenolide (PyrPT) | Parthenolide (30 mg), pyrrolidine (0.2 mL), triethylamine (0.2 mL), ethanol (5 mL) | Refluxing 12 hours | 80 | 5 μM, 23%<br>10 μM, 85%<br>20 μM, 95% |
| 11S,11,13-Dihydro, 13-(piperidin-1-yl)parthenolide (PipPT) | Parthenolide (250 mg), piperidine (1 mL), triethylamine (5 mL), ethanol (100 mL) | Refluxing overnight | 86 | 2.5 μM, 71%<br>5 μM, 91% |
| 11S,11,13-Dihydro, 13-(morpholin-1-yl)parthenolide (MorPT) | Parthenolide (100 mg), morpholine (0.5 mL), triethylamine (2 mL), ethanol (30 mL) | Refluxing overnight | 91 | 5 μM, 5%<br>20 μM, 20% |
| 11S,11,13-Dihydro, 13-(4-methylpiperidin-1-yl)parthenolide (4MePipPT) | Parthenolide (100 mg), 4-methylpiperidine (0.5 mL), triethylamine (2 mL), ethanol (30 mL) | Refluxing overnight | 89 | 10 μM, 83% |
| 11S,11,13-Dihydro, 13-(4-methylpiperazin-1-yl)parthenolide (4MePizPT) | Parthenolide (30 mg), 4-methylpiperazine (0.2 mL), triethylamine (1 mL), ethanol (20 mL) | Refluxing overnight | 74 | 10 μM, 7% |
| 11S,11,13-Dihydro, 13-(homopiperidin-1-yl)parthenolide (HomoPipPT) | Parthenolide (100 mg), homopiperidine (500 mg), triethylamine (2 ml), ethanol (30 ml) | Refluxing overnight | 82 | 10 μM, 40% |
| 11S,11,13-Dihydro, 13-(heptamethyleneimin-1-yl)parthenolide (HeptaMePipt) | Parthenolide (100 mg), heptamethyleneimin (500 mg), triethylamine (2 mL), ethanol (30 mL) | Refluxing overnight | 74 | 10 μM, 10% |
| 11S,11,13-Dihydro, 13-(azetidin-1-yl)parthenolide (AzePT) | Parthenolide (100 mg), azetidine (100 mg), triethylamine (2 mLl), ethanol (20 mL) | Stirred at room temperature 2 days | 93 | |
| 11S,11,13-Dihydro, 13-diallylamino-parthenolide | Parthenolide (100 mg), diallylamine (200 mg), triethylamine (2 mL), ethanol (30 mL) | Refluxing overnight | 57 | |
| 11S,11,13-Dihydro, 13-Methylbutyl amino-parthenolide | Parthenolide 25 mg Methylbutylamine 20 mg Methanol, 8 hrs | Room temperature with stirring | 85% | 10 μM, 68% |
| 11S,11,13-Dihydro, 13-Methyl pentyl amino parthenolide | Parthenolide 25 mg Methylpentylamine 20 mg Methanol, 6 hrs | Room temperature with stirring | 88% | 10 μM, 45% |
| 11S,11,13-Dihydro, 13-ethylamino parthenolide | Parthenolide 25 mg Ethylamine 90 mg Methanol, 5 hrs | Room temperature with stirring | 90% | 10 μM, 2% |
| 11S,11,13-Dihydro, 13-methylamino parthenolide | Parthenolide 25 mg, 2M Methylamine in methanol (1 ml), Methanol, 5 hrs | Room temperature with stirring | 93% | 10 μM, 4% |
| 11S,11,13-Dihydro, 13-cyclopropylamino parthenolide | Parthenolide 25 mg Cyclopropylamine 20 mg Methanol, 6 hrs | Room temperature with stirring | 90% | 10 μM, −6% |
| 11S,11,13-Dihydro, 13-propargylamino parthenolide | Parthenolide 25 mg Propargylamine 20 mg Methanol, 6 hrs | Room temperature with stirring | 82% | 10 μM, 7% |

TABLE 2

Aminoparthenolide salts and their antileukemic activity

| Compound | Reactants and Solvent | Reaction Conditions | Yield (%) | Antileukemic activity |
|---|---|---|---|---|
| 11S,11,13-Dihydro, 13-dimethylamino-parthenolide hydrochloride | 11S,11,13-Dihydro, 13-dimethylamino-parthenolide (10 mg), HCl in ether (1M, 0.03 mL) | Refrigerator, 24 hours | 72 | |
| 11S,11,13-Dihydro, 13-(pyrrolidin-1-yl)parthenolide hydrochloride | 11S,11,13-Dihydro, 13-(pyrrolidin-1-yl)parthenolide (5 mg), HCl in ether (1M, 0.015 mL) | Refrigerator, 24 hours | 10 | 10 μM, 85% |
| 11S,11,13-Dihydro, 13-(piperidin-1-yl)parthenolide hydrochloride | 11S,11,13-Dihydro, 13-(piperidin-1-yl)parthenolide (5 mg), HCl in ether (1M, 0.015 mL) | Refrigerator, 24 hours | 18 | 10 μM, 88% |
| 11S,11,13-Dihydro, 13-(4-methylpiperidin-1-yl)parthenolide hydrochloride | 11S,11,13-Dihydro, 13-(4-methylpiperidin-1-yl)parthenolide (50 mg), HCl in ether (1M, 0.15 mL) | Refrigerator, 4 days | 38.3 | 10 μM, 62% |
| 11S,11,13-Dihydro, 13-dimethylamino-parthenolide maleate | 11S,11,13-Dihydro, 13-dimethylamino-parthenolide (30 mg), maleic acid (12 mg), ethanol (8 mL) | Room temperature for 1 week | 55 | |
| 11S,11,13-Dihydro, 13-dimethylamino-parthenolide methiodide | 11S,11,13-Dihydro, 13-dimethylamino-parthenolide (30 mg), added iodomethane (90 mg), methanol (6 mL) | Room temperature for 3 days | 86 | |
| 11S,11,13-Dihydro, 13-(4-methylpiperidin-1-yl)parthenolide methiodide | 11S,11,13-Dihydro, 13-(4-methylpiperidin-1-yl)parthenolide (70 mg), iodomethane (200 mg), methanol (12 mL) | Room temperature for 3 days | 79 | |
| 11H,13-(N,N-Dimethylamino)-dehydrocostuslactone | | | | 10 μM, 12% |
| 11H,13-(N-Piperidine)-dehydrocostuslactone | | | | 10 μM, 14% |
| 11H,13-(N-Butyl-N-methylamino)-dehydrocostuslactone | | | | 10 μM, 8% |
| 11H,13-(N-Propylamino)-dehydrocostuslactone | | | | 10 μM, 24% |
| 11H,13-(N-Diallyl)-dehydrocostuslactone | | | | 10 μM, 2% |
| 11H,13-(N-Morpholine)-dehydrocostuslactone | | | | 10 μM, 10% |
| 11H,13-(N-Pyrrolidine)-dehydrocostuslactone | | | | 10 μM, 20% |
| 11H,13-(N-Ethyl-N-benzyl)-dehydrocostuslactone | | | | 10 μM, 13% |
| 11H,13-(N-Methyl-N-propylamino)-dehydrocostuslactone | | | | 10 μM, 1% |
| 11H,13-(N,N-Diethylamino)-dehydrocostuslactone | | | | 10 μM, 5% |
| 11H,13-(N-Methyl-N-pentylamino)-dehydrocostuslactone | | | | 10 μM, 0% |

Example 10

Analysis of Parthenolide and Dimethylaminoparthenolide (DMAPT) Using Human-Mouse Xenografts To assess the effect of parthenolide on primary human stem cell populations, experiments were conducted using transplantation into immune deficient NOD/SCID mice. Successful engraftment of NOD/SCID bone marrow at 6-8 weeks post-transplant has been shown to be a measure of stem cell content for human hematopoietic cell populations (Lapidot et al., *J Mol. Med.* 1997; 75: 664-673; Dick, *Curr Opin Hematol.* 1996; 3:405-409). For each experiment, cryopreserved mononuclear cell specimens from normal or AML donors were thawed, and treated in vitro with 7.5 micromolar parthenolide for 12-18 hours. Following culture, 5-10 million cells/animal were injected intravenously into sublethally irradiated (300 Rad) NOD/SCID mice. After 6-8 weeks, animals were sacrificed and bone marrow was analyzed for the presence of human cells using flow cytometry as previously described (Guzman et al., *Proc Natl Acad Sci USA* 2002; 99: 16220-162253). Human specific antibodies for CD45 were used to assess the level of total engraftment.

In three independent experiments, the level of engraftment for parthenolide-treated AML cells was dramatically reduced, which indicates a direct effect on the AML stem cell compartment. In contrast, no reduction in engraftment was detected for parthenolide-treated normal specimens, thus showing the parthenolide does not target normal hematopoietic stem cells. Similarly, treatment of AML cells with 7.5 micromolar DMAPT also yielded a strong reduction in NOD/SCID engraftment while treatment of normal cells showed no significant effects.

Example 11

MTS-PMS Assay

A 96-well U-bottomed plate (Becton Dickinson Labware, Franklin Lakes, N.J.) at a concentration of 5,000 cells per 50 microliters (mL) of media was incubated in 5% $CO_2$ at 37° C. for 24 hours. Varying compound concentrations in 50 mL of media were added to the media 24 hours later. Colorimetric readings were obtained using the MTS/PMS system and an ELISA plate reader, after 48 hours of exposure to DMAPT. The readings obtained for each concentration tested were from an average of eight wells. Each experiment was expressed as a percentage of the solvent control and completed at least three times with consistent results. The results presented are an average of three experiments. The hormone refractory prostate cancer cell line CWR22Rv1 was treated with increasing concentrations of parthenolide and DMAPT. for three hours Both parthenolide and DMAPT reduced cellular proliferation by 50% at 5 μm in the CWR22 MTS-PMS assay. Cellular proliferation was also measured in the MTS-PMS assay using four lung cancer cell lines treated with parthenolide and derivatives PIPT ((11S,11,13-dihydro, 13-(piperidin-1-yl)parthenolide), 4MEPT (11S,11,13-dihydro, 13-(4-methylpiperidin-1-yl)parthenolide) and MAPT (11S, 11,13-dihydro, 13-dimethylaminoparthenolide). Parthenolide and its derivatives inhibited cellular proliferation in a dose dependent manner between 2 and 10 μM with 70% inhibition at 10 μM in A549, 50% in H460, 40% in H-23 and 40% in H522 (FIGS. 2-5).

Example 12

Clonogenic Assay

Figure 6:
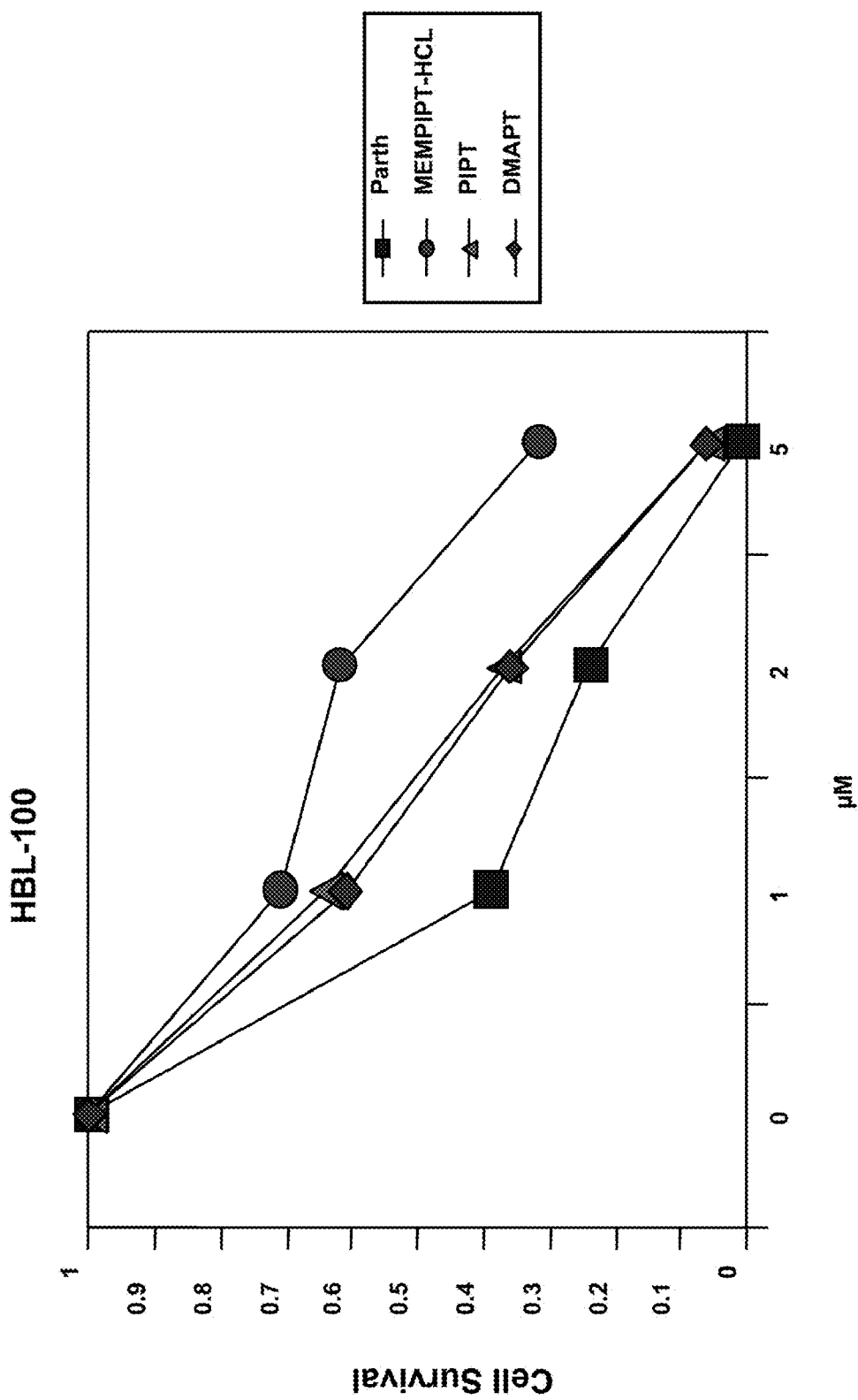
FIG. 6 shows the effectiveness of parthenolide and derivatives of the present invention against breast cancer cell line HBL-100 in a clonogenic assay.
Figure 7:
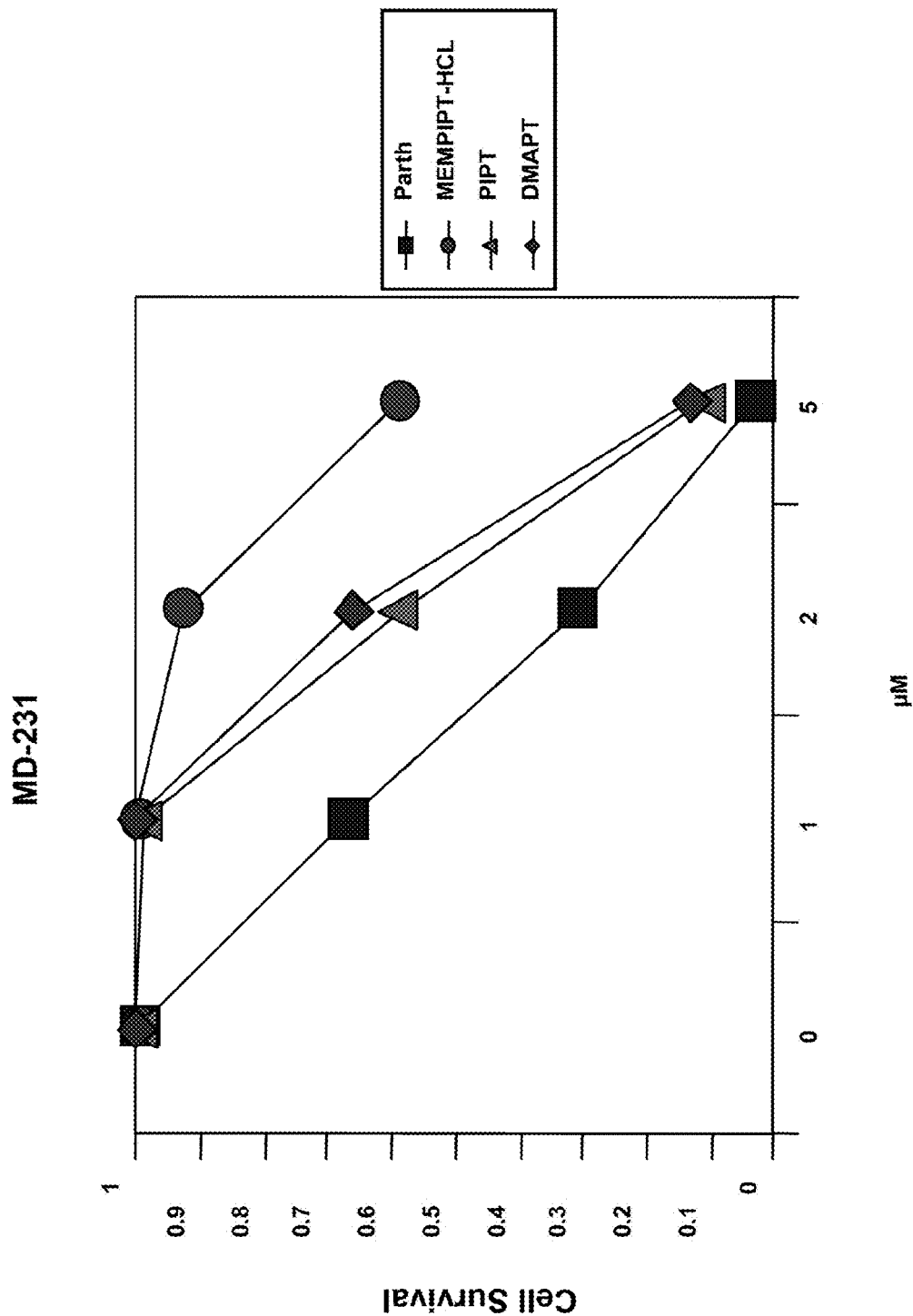
FIG. 7 shows the effectiveness of parthenolide and derivatives of the present invention against breast cancer cell line MD-231 in a clonogenic assay.
Figure 8:
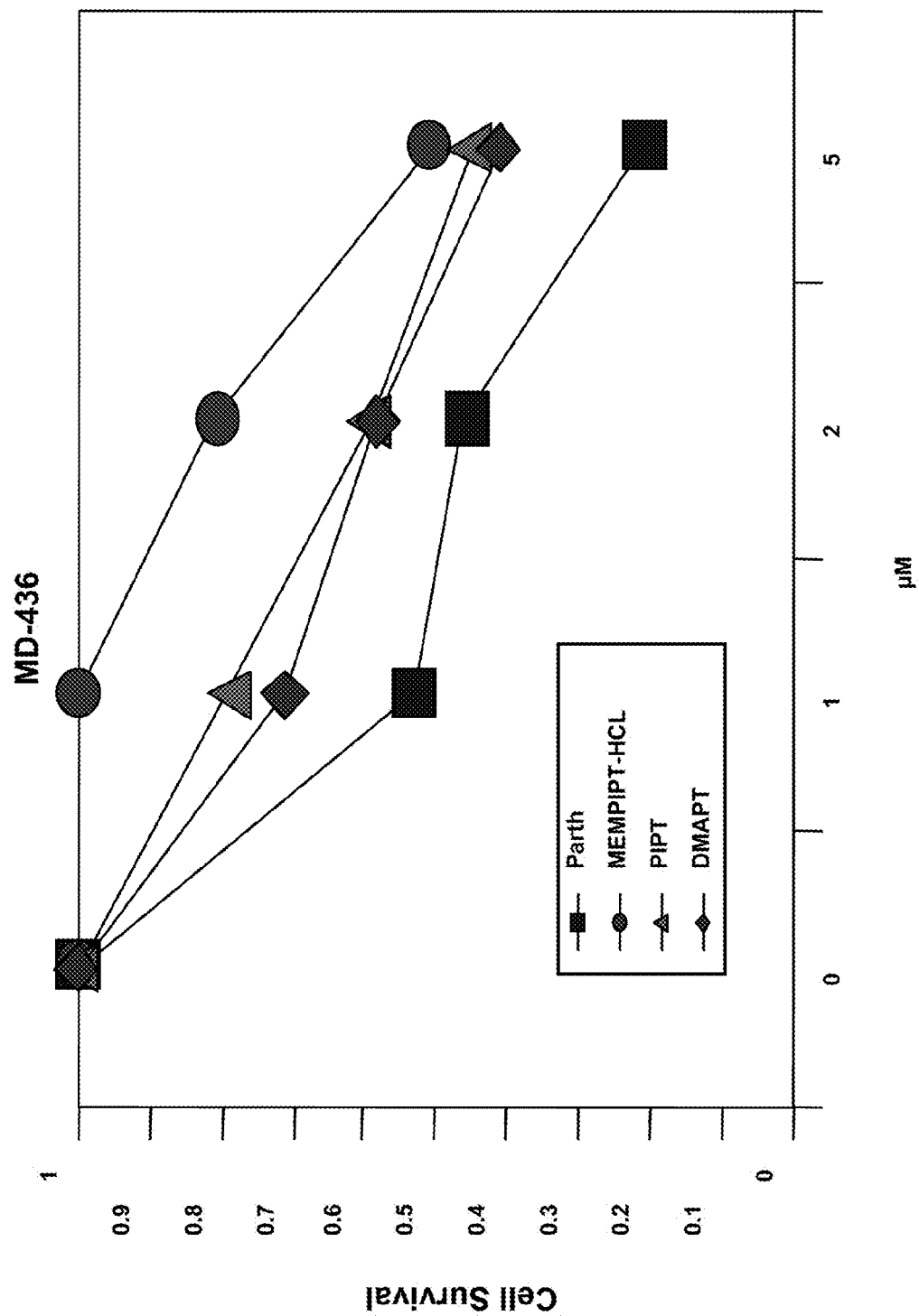
FIG. 8 shows the effectiveness of parthenolide and derivatives of the present invention against breast cancer cell line MD-436 in a clonogenic assay
Figure 9:
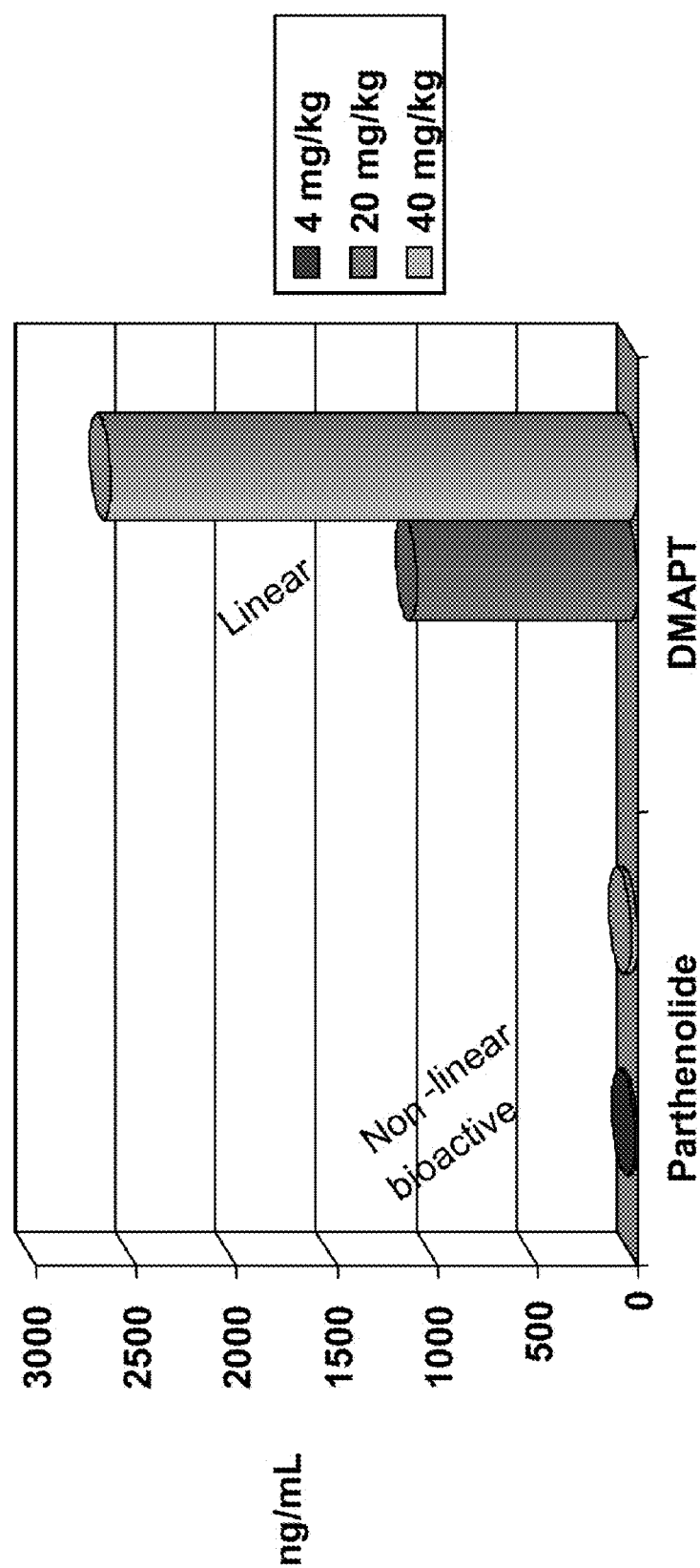
FIG. 9 shows parthenolide and DMAPT plasma concentrations at one hour following oral gavage in mice.

Initially, 100 cells growing in log phase were plated per 3 ml of media in each well of a six well plate. After 24 hrs of plating of the cells the test compound was added at varying concentrations. At 24 and 96 hours after addition of drug, the media was changed. Hence, the cells were only exposed to the drug for 24 hrs. When cell colonies appeared at Day 15 they were stained by Sure Stain Dye and counted. The hormone refractory prostate cancer cell line CWR22Rv1 was treated with increasing concentrations of parthenolide derivatives DMAPT, PIPT and 4MEPT for three hours. Cellular proliferation was reduced by up to 80% at 2 μm in the clonogenic assay (FIG. 1). The breast cancer cell line clonogenic assay with hbl-100, mdl-231 and 436 cells showed almost complete inhibition of proliferation with DMAPT at 2 μm concentration in the clonogenic assay (FIGS. 6-8). Parthenolide also reduced proliferation with similar dosage ranges.

Example 13 cDNA Array Analysis

Total cellular RNA was extracted from the human monocyte cell line THP-1 under three conditions 2 hours after Time 0:
1) Control was added at Time 0
2) Lipopolysacchride (10 nM) was added at Time plus one (1) hour
3) At Time 0, 10 micromoles of DMAPT was added and then at Time+1 LPS (10 nM) was added.

RNA was extracted using RNeasy Min Kit (Qiagen, USA) according to the manufacturer's instructions. The Human Drug Targets for Inflammation and Immunomodulation Q series GE array kit (HS-048-12) was obtained from SuperArray Bioscience Corporation (Frederick, Md.). The kit determines expression of 96 genes that are associated with inflammation. RNA from respective samples was used as a template to generate biotin labeled cDNA probes using GEArray Ampolabelling RT kit (SuperArray, Bioscience Corp., USA). The cDNA probes corresponding to the mRNA population were then denatured and hybridization was carried out in GEHyb solution to nylon membranes spotted with gene specific fragments. Membranes were then washed in 2×SSC, 1% SDS twice for 15 minutes each, followed by 0.1 SSC, 0.5% SDS twice for minutes each. Chemiluminescence was used to visualize the expression levels of each transcript and the results were quantified with the GEArray Analyzer. The change in a given gene transcript was estimated by normalizing the signal intensities with the signal derived from PPIA and with minimum background subtraction.

As can be seen in Table 3, transcription of 25 genes was increased after pre-treatment with LPS. More importantly pretreatment with DMAPT prevented or blunted the increase in gene transcription induced by LPS. For example, the transcription of tumor necrosis factor (TNF), released in septic shock, is increased by 3 fold (298%) when treated with LPS. Pretreatment with DMAPT however prevents transcription of LPS and in fact decreases its production to 2% of control. Similarly, transcription of cyclo-oxygenase-2, the target of classical non-steroidal anti-inflammatory agents, was increased 1.5 fold (150%). In the presence of DMAPT, the gene expression not only prevented the increase by LPS but decreased it to 30% (0.7) of solvent control. DMAPT therefore may act to decrease inflammation by decreasing cytokines as evidenced by decreased genes in human monocytes

TABLE 3 cDNA Array Analysis

| Gene | LPS Treatment for 1 hour: % Change of Gene | DMAPT Pre-treatment for 2 hours then 1 hour Treatment of LPS % Change of Genes |
|---|---|---|
| CD28 antigen (Tp44) | 23 | 0.814 |
| CD3G antigen, gamma polypeptide (TiT3 complex) | 14 | 0.6 |

TABLE 3-continued cDNA Array Analysis

| Gene | LPS Treatment for 1 hour: % Change of Gene | DMAPT Pre-treatment for 2 hours then 1 hour Treatment of LPS % Change of Genes |
|---|---|---|
| Colony stimulating factor 2 (granulocyte-macrophage) | 26 | 0.926 |
| Intercellular Adhesion Molecule 1 | 257 | 58 |
| Interleukin 13 | 93 | 0.64 |
| Interleukin 1 receptor, type I | 10 | 0.33 |
| Interleukin 1 receptor, type II | 326 | 0.74 |
| Nitric oxide synthase 2A (inducible) | 226 | 48 |
| Phosphodiesterase 4A, cAMP-specific | 14 | 0.46 |
| Phosphodiesterase 4B, cAMP-specific | 220 | 0.59 |
| Phospholipase A2, group IB (pancreas) | 114 | 0.57 |
| Phospholipase A2, group IVC | 350 | 0.89 |
| Phospholipase A2, group VII | 129 | 0.05 |
| Phospholipase C, gamma 1 | 342 | 0.24 |
| Peroxisome proliferative activated receptor, gamma | 49 | 0.48 |
| Platelet-activating factor receptor | 32 | 0.002 |
| Prostaglandin D2 receptor (DP) | 35 | 0.17 |
| Prostaglandin F receptor (FP) | 879 | 1.46 |
| Cyclooxygenase 1 | 176 | 0.731 |
| Cyclooxygenase 2 | 152 | 0.7 |
| Thromboxane A synthase 1 | 283 | 0.07 |
| Tumor necrosis factor (TNF superfamily, member 2) | 298 | 0.02 |
| Tumor necrosis factor (ligand) superfamily, member 13b | 217 | 0.89 |
| Tumor necrosis factor (ligand) superfamily, member 5 | 692 | 23 |
| Vascular cell adhesion molecule 1 | 154 | 0.02 |

Example 14

Oral Bioavailability in Mice

Figure 4:
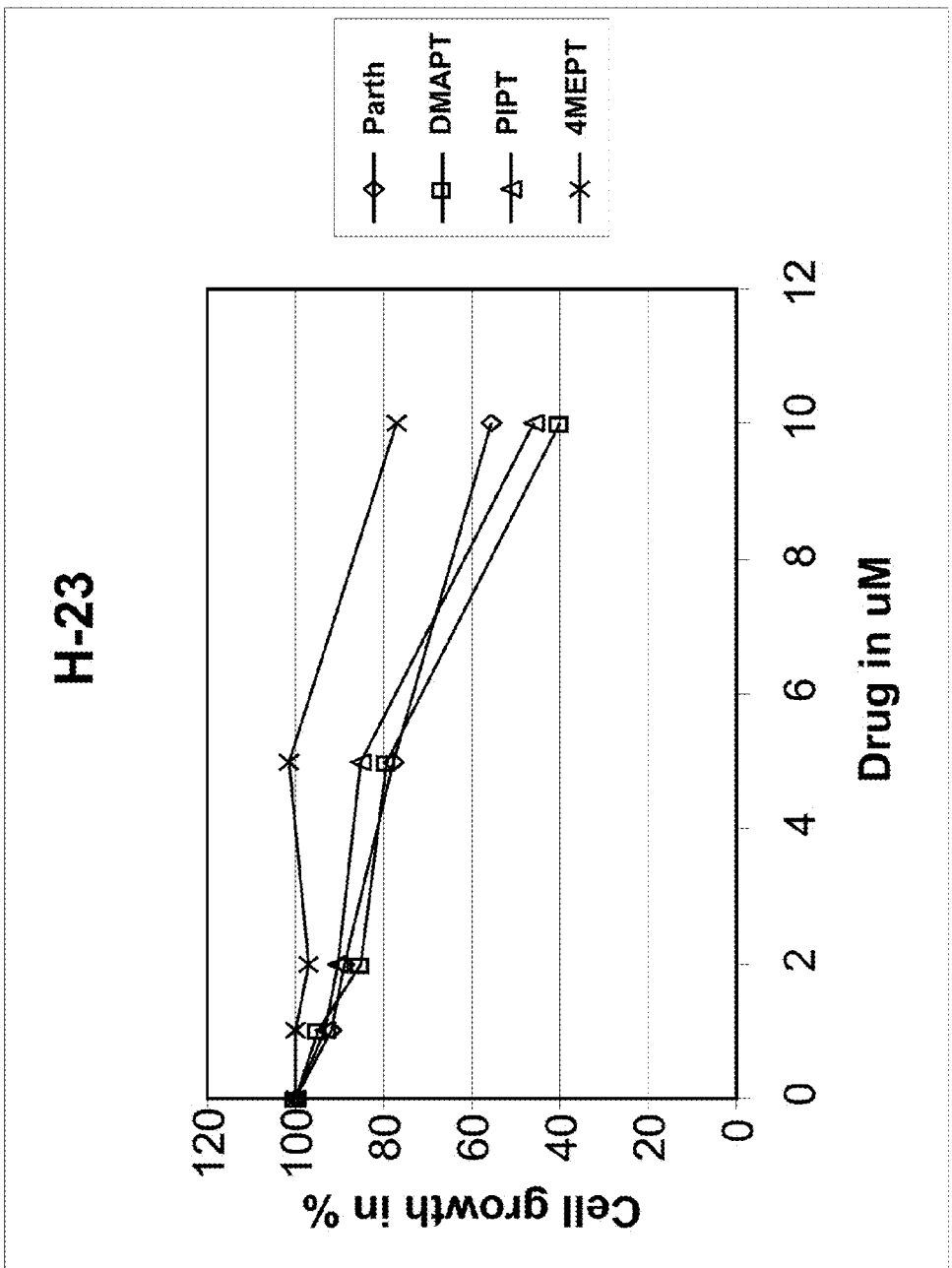
FIG. 4 shows the effectiveness of parthenolide and derivatives of the present invention against lung cancer cell line H-23 in a cellular proliferation MTS-PMS assay.
Figure 5:
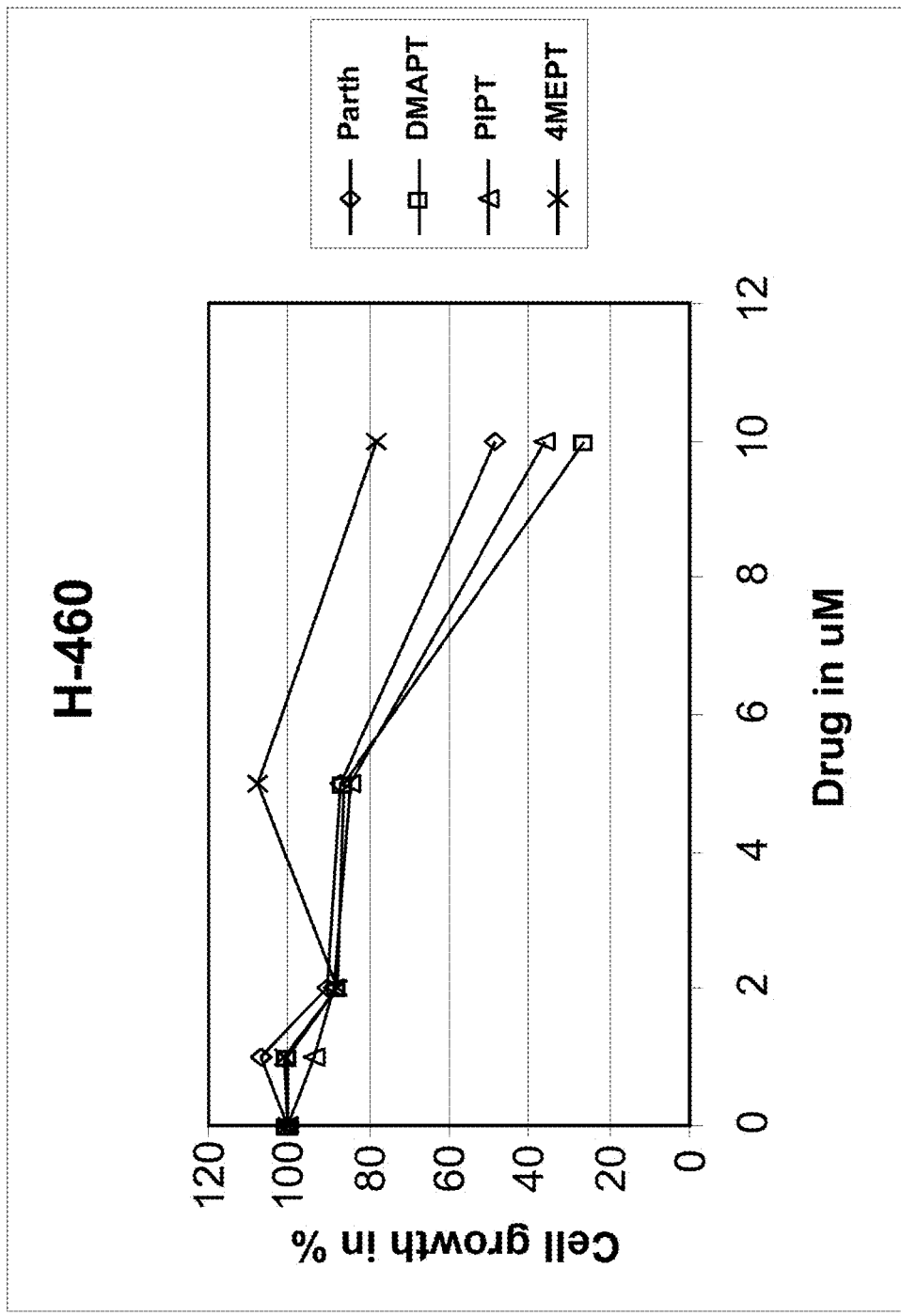
FIG. 5 shows the effectiveness of parthenolide and derivatives of the present invention against lung cancer cell line H-460 in a cellular proliferation MTS-PMS assay.

Preliminary in vivo work was conducted to determine the bioavailability and toxicity of this agent in mice. As shown in FIG. 4 it was demonstrated that whereas 40 mg/kg of oral parthenolide provided a plasma level one hour after oral gavage of only ~200 nM, the same dose of DMAPT provided a plasma level of ~2500 ng/mL (ie 8 μM —average of 5 mice in each group; measured by LC-MS). Given the concern from providing such a high plasma concentration we completed a preliminary toxicity study that showed the mice gained weight and survived three weeks of daily treatment with oral DMAPT at 40 mg/kg with no overt toxicities.

Example 15

Electrophoretic Mobility Gel Shift Assay

Each cancer cell line in exponential growth phase was treated with solvent control or various concentrations of parthenolide derivatives dissolved in 100% ethanol for 3 hours prior to harvesting. Cells were harvested and whole cell extracts were prepared as described previously (Nakshatri et al., Mol Cell Biol, 17: 3629-3639, 1997; Sweeney et al., Clin Cancer Res, 10: 5501-5507, 2004). Extracts were incubated with a radiolabelled NFκB probe for 30 minutes at room temperature. The oligonucleotide probe binds to the NFκB DNA binding site in the promoter region of the immunoglobulin gene. Electrophoresis and autoradiography were performed as described previously (Nakshatri et al., 1997) using NFκB and SP-1 probes (Promega, Madison, Wis.). The specificity of parthenolide and derivative inhibition of NFκB DNA binding was verified by the use of the SP-1 probe as a control. Identification of the NFκB subunits binding to DNA and inhibited by DMAPT were identified by gel supershift. Constitutive NF-κB DNA binding activity was determined in the lung cancer cell lines A-549, H-23, H-522, and H-460. All four non-small lung cancer cells were treated with increasing concentrations of DMAPT for three hours, and NF-κB DNA binding was measured by electrophoretic mobility shift assay (EMSA) as described. NF-κB DNA binding activity was highest in A-549 cells, followed by H-23, H-522 and H-460 cells. DMAPT between 2 and 10 micromolar substantially decreased NF-κB DNA binding activity in all lung cancer cell lines tested.

Figure 10:
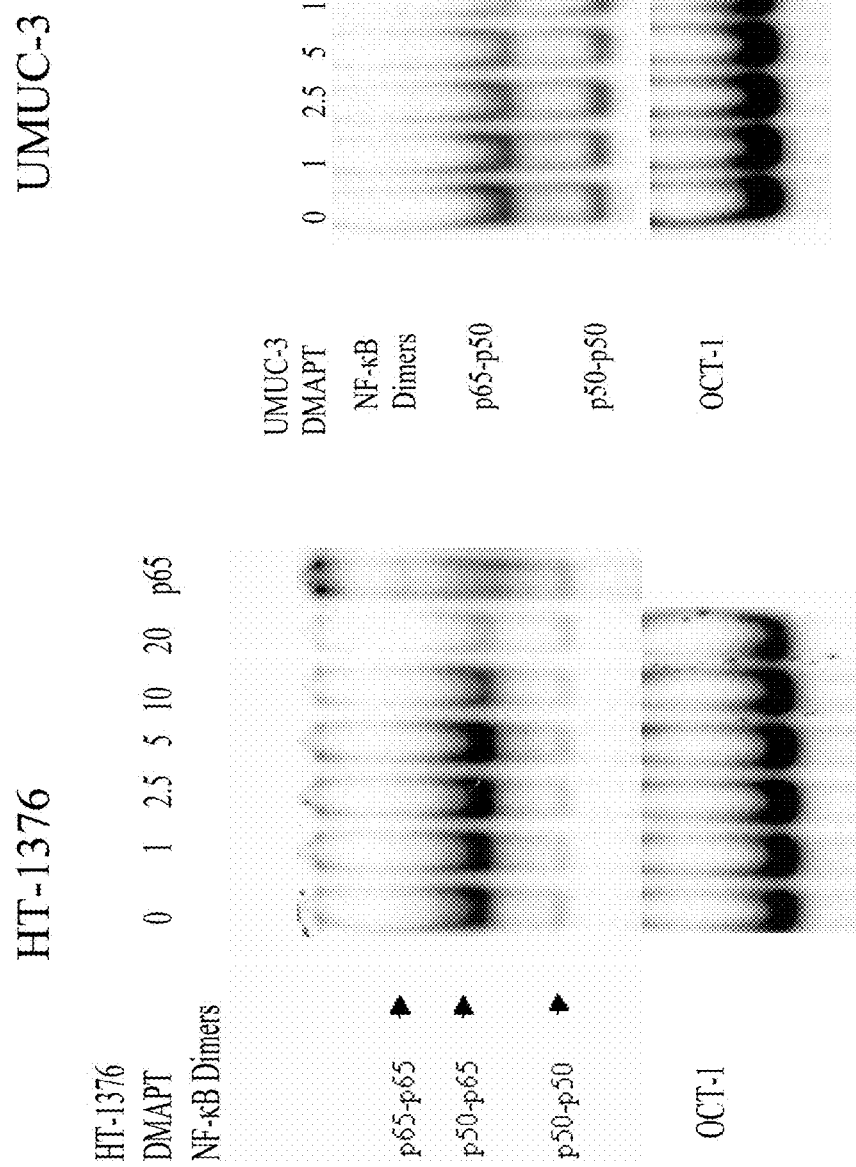
FIG. 10 shows DMAPT dose-dependent inhibition of NF-kB DNA binding in two transitional cell carcinoma cell lines HT-1376 and UMUC-3 in electrophoretic mobility gel shift assay (EMSA).

Cancer cell lines HT-1376 and UMUC-3 were treated with increasing concentrations of DMAPT for three hours. Whole cell extracts were prepared as described and DNA binding by NF-κB was analyzed by EMSA with NF-κB and OCT-1 (internal control) probes. DMAPT decreased NF-κB DNA binding in a dose-dependent manner with HT-1376 and UMUC-3 cell lines (FIG. 10).

The hormone refractory prostate cancer cell line, CWR22Rv1 was treated with increasing concentrations of DMAPT for three hours. Whole cell extracts were prepared as described and DNA binding by NF-κB was analyzed by EMSA with NF-κB and SP-1 (internal control) probes. DMAPT decreased NF-κB DNA binding in a dose dependent manner with substantial decreases of NF-κB DNA binding at 10 μM DMAPT.

EMSA results thus showed DMAPT decreased the constitutive NF-κB DNA binding in several cancer cell lines.

Example 16

Pretreatment of Radiation Sensitive Cell Line A549

The radiation sensitive cell line A549 was pretreated with parthenolide concentrations ranging from 0 to 2.5 micromolar. The cells were then subjected to ionizing radiation doses ranging from 0-6 Gy and survival fraction of the cells determined. Results demonstrated that parthenolide induced radiation sensitivity to the cells in a dose-dependent manner with survival fraction at 2.5 micromolar ranging from 10% at 2 Gy to less than 1% at 6 Gy. Cells not receiving pre-treatment with parthenolide had greater than 50% survival fraction at the highest radiation dose of 6 Gy and over 90% survival at 2 Gy.

Example 17

TRAIL Induced Apoptosis Assay

MDA-MB-231 breast cancer cells (2×105 cells in 60 mm plates) were treated first with 2 or 5 μM of DMAPT (LC-1).

Figure 11:
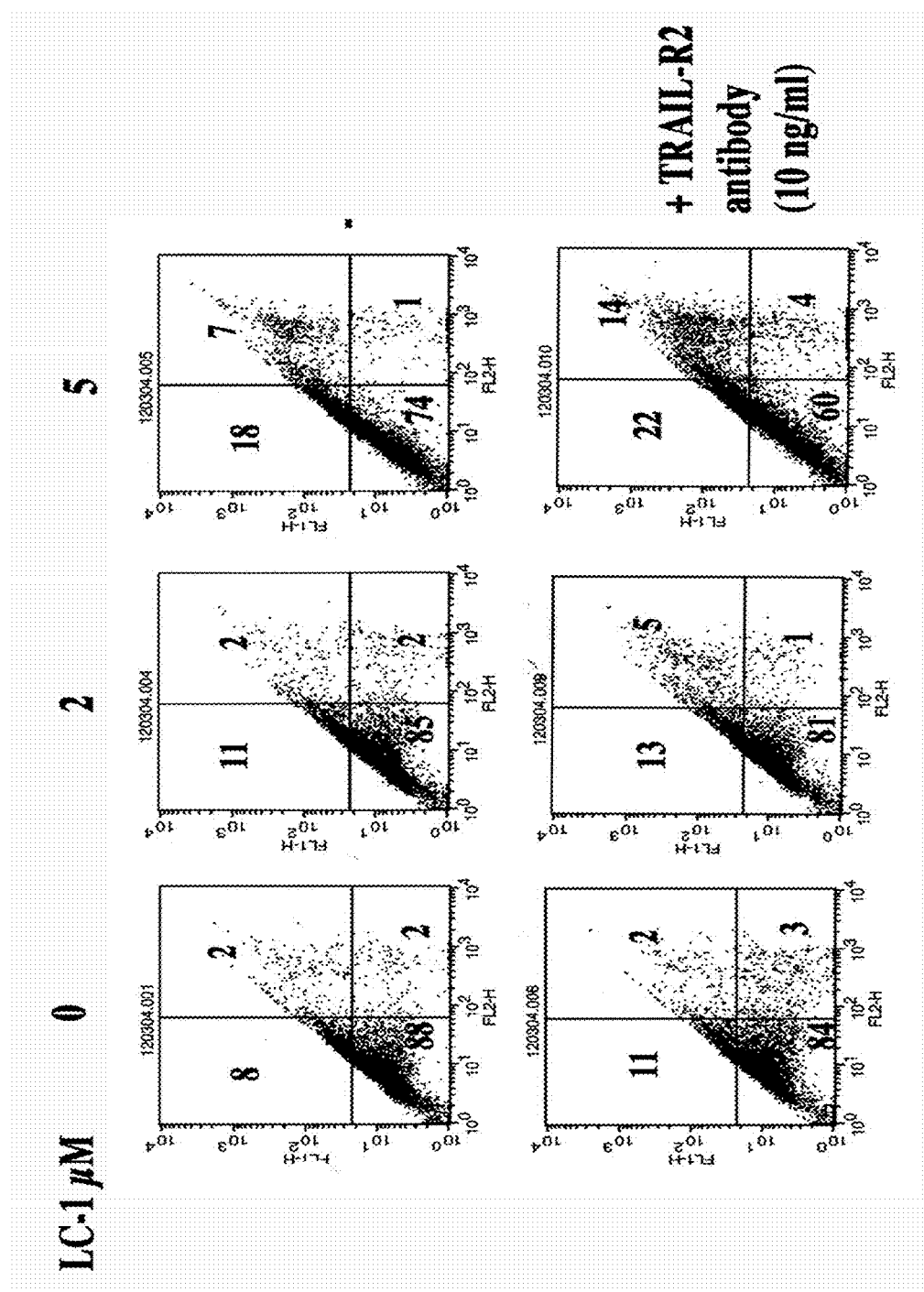
FIG. 11 shows FSCScan analysis of TRAIL induced apoptosis assay using MDA-MB-231 breast cancer cells treated first with DMAPT, then TRAIL-RII-activating antibodies.
Figure 12:
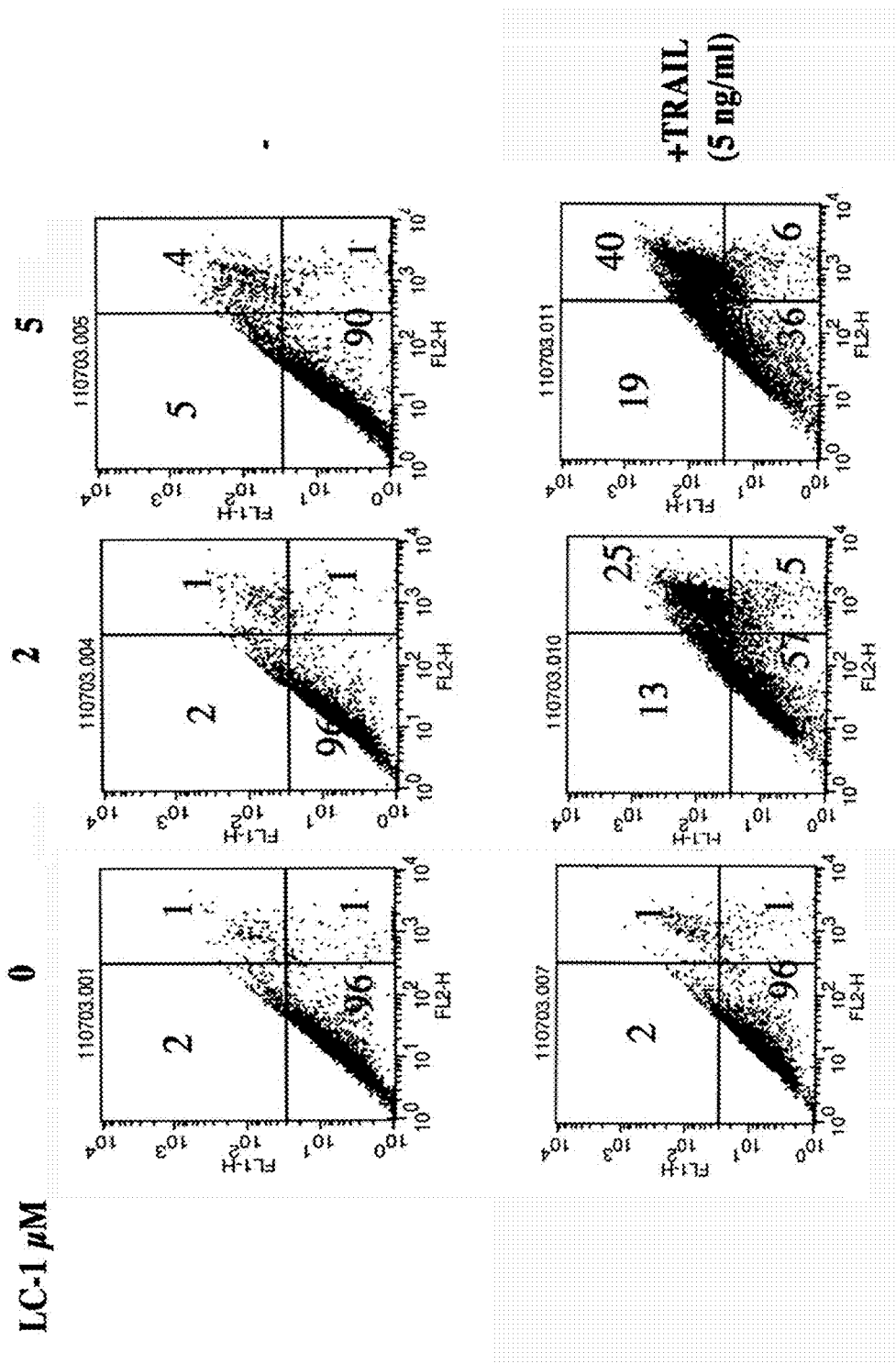
FIG. 12 shows FSCScan analysis of TRAIL induced apoptosis assay using MDA-MB-231 breast cancer cells treated first with DMAPT, then TRAIL.

After two hours, TRAIL (TNF related-apoptosis-inducing-ligand, 5 ng/ml) or TRAIL-RII-activating antibodies (10 ng/ml) were added. After 48 hours of TRAIL or TRAIL-RII antibody treatment, cells were harvested and apoptosis was measured using carboxyfluorescein-FLICA assay. Briefly, both attached and floating cells were collected by trypsinization, incubated with carboxyfluorescein-labeled pan-caspase inhibitor FAM-VAD-FMK for 2 h at 37° C. Labeled cells were rinsed twice in PBS and resuspended in 300 µl of PBS containing 0.3 µg of propidium iodide. Apoptotic cells were identified by FACScan analysis. Live cells do not stain (FIGS. 11 and 12) Lower left quadrant). FAM-VAD-FMK stains apoptotic cells (upper left). Apoptotic cells that have lost plasma membrane integrity are stained by both FAM-VAD-FMK and propidium iodide (upper right). Necrotic cells are stained only by propidium iodide (lower right). MDA-MB-231 cells are relatively resistant to TRAIL. However, they became sensitive to TRAIL or TRAIL-RII activating antibody-induced apoptosis and atypical apoptosis upon pretreatment with DMAPT.

We claim:

1. A method of treatment of bone marrow in the treatment of leukemia, comprising administering to a mammal afflicted with leukemia, an effective amount of a compound of formula (I):

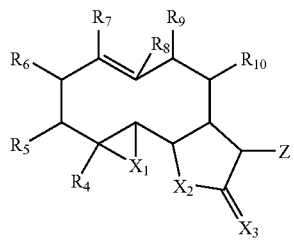

wherein:

$X_1$, $X_2$ and $X_3$ are O;

$R_5$, $R_6$, $R_7$, $R_9$, and $R_{10}$ are H, and $R_4$ and $R_8$ are methyl; and Z is —$CH_2R^*$ wherein $R^*$ is an amino acid residue bonded to the Z methylene via a nitrogen or a sulfur atom; or $R^*$ is —$NR^1CO_2$—$R^2$, —$NR^1C(O)NR^2$, —$NR^1R^2$, or —$N^+R^1R^2R^{11}Y^-$ wherein $R^1$ and $R^2$ are independently selected from H, CN, and optionally substituted straight-chained or branched aliphatic optionally containing 1 or more double or triple bonds; wherein optional substituents are selected from one or more of —$NH_2$, —$NH(C_{1-4}$ aliphatic), —$N(C_{1-4}$ aliphatic)$_2$, halogen, —OH, —O—($C_{1-4}$ aliphatic), —$NO_2$, —CN, —$CO_2H$, —$CO_2(C_{1-4}$ aliphatic), —O(halo $C_{1-4}$ aliphatic), or -halo($C_{1-4}$ aliphatic); wherein each $C_{1-4}$ aliphatic is optionally substituted; or $R^1$ and $R^2$ are independently selected from cycloalkyl, heterocycloalkyl, aryl or heteroaryl; and provided that $R^1$ and $R^2$ are not simultaneously H; or where $R^*$ is $NR^1R^2$, $R^1$ and $R^2$ optionally together with the nitrogen atom form an optionally substituted 5-12 membered ring, said ring optionally comprising 1 or more heteroatoms or a group selected from —CO—, —SO—, and —$SO_2$—;

$R^{11}$ is selected from H or $C_{1-4}$ aliphatic; and $Y^-$ is selected from the group consisting of fluoride, chloride, bromide, iodide, sulfate, nitrate, bicarbonate, carbonate, acetate, citrate, malonate, tartarate, succinate, benzoate, ascorbate, alpha-ketoglutarate, alpha-glycerophosphate, methylsulfonate, toluenesulfonate, and benzenesulfonate; or a pharmaceutically acceptable salt thereof.

2. A method of treatment of bone marrow in the treatment of leukemia comprising contacting said bone marrow in vitro or in vivo with an effective amount of a compound of formula (I):

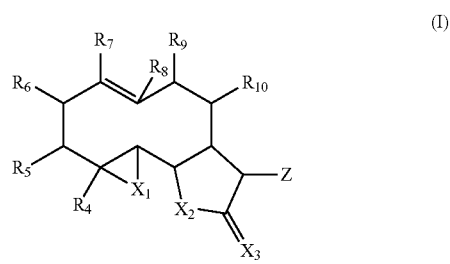

wherein:

$X_1$, $X_2$ and $X_3$ are O;

$R_5$, $R_6$, $R_7$, $R_9$, and $R_{10}$ are H, and $R_4$ and $R_8$ are methyl; and Z is —$CH_2R^*$ wherein $R^*$ is an amino acid residue bonded to the Z methylene via a nitrogen or a sulfur atom; or $R^*$ is —$NR^1CO_2$—$R^2$, $R^1$ and $R^2$ are independently selected from H, CN, and optionally substituted straight-chained or branched aliphatic optionally containing 1 or more double or triple bonds; wherein optional substituents are selected from one or more of —$NH_2$, —$NH(C_{1-4}$ aliphatic), —$N(C_{1-4}$ aliphatic)$_2$, halogen, —OH, —O—($C_{1-4}$ aliphatic), —$NO_2$, —CN, —$CO_2H$, —$CO_2(C_{1-4}$ aliphatic), —O(halo $C_{1-4}$ aliphatic), or -halo($C_{1-4}$ aliphatic); wherein each $C_{1-4}$ aliphatic is optionally substituted; or $R^1$ and $R^2$ are independently selected from cycloalkyl, heterocycloalkyl, aryl or heteroaryl; and provided that $R^1$ and $R^2$ are not simultaneously H; or where $R^*$ is $NR^1R^2$, $R^1$ and $R^2$ optionally together with the nitrogen atom form an optionally substituted 5-12 membered ring, said ring optionally comprising 1 or more heteroatoms or a group selected from —CO—, —SO—, and —$SO_2$—;

$R^{11}$ is selected from H or $C_{1-4}$ aliphatic; and $Y^-$ is selected from the group consisting of fluoride, chloride, bromide, iodide, sulfate, nitrate, bicarbonate, carbonate, acetate, citrate, malonate, tartarate, succinate, benzoate, ascorbate, alpha-ketoglutarate, alpha-glycerophosphate, methylsulfonate, toluenesulfonate, and benzenesulfonate; or a pharmaceutically acceptable salt thereof.

3. A method of treating bone marrow in human bone marrow transplant treatment of leukemia, the method comprising treating bone marrow prior to reintroduction of bone marrow to patient with an effective amount of a compound of formula (I):

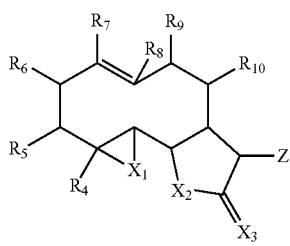

(I)

wherein:
$X_1$, $X_2$ and $X_3$ are O;
$R_5$, $R_6$, $R_7$, $R_9$, and $R_{10}$ are H, and $R_4$ and $R_8$ are methyl; and
Z is —$CH_2R^*$ wherein $R^*$ is an amino acid residue bonded to the Z methylene via a nitrogen or a sulfur atom; or $R^*$ is —$NR^1CO_2$—$R^2$, —$NR^1C(O)NR^2$, —$NR^1R^2$, or —$N^+R^1R^2R^{11}Y^-$ wherein
$R^1$ and $R^2$ are independently selected from H, CN, and optionally substituted straight-chained or branched aliphatic optionally containing 1 or more double or triple bonds; wherein optional substituents are selected from one or more of —$NH_2$, —$NH(C_{1-4}$ aliphatic), —$N(C_{1-4}$ aliphatic$)_2$, halogen, —OH, —O—($C_{1-4}$ aliphatic), —$NO_2$, —CN, —$CO_2H$, —$CO_2(C_{1-4}$ aliphatic), —O(halo $C_{1-4}$ aliphatic), or -halo($C_{1-4}$ aliphatic); wherein each $C_{1-4}$ aliphatic is optionally substituted; or $R^1$ and $R^2$ are independently selected from cycloalkyl, heterocycloalkyl, aryl or heteroaryl; and provided that $R^1$ and $R^2$ are not simultaneously H; or where $R^*$ is $NR^1R^2$, $R^1$ and $R^2$ optionally together with the nitrogen atom form an optionally substituted 5-12 membered ring, said ring optionally comprising 1 or more heteroatoms or a group selected from —CO—, —SO—, and —$SO_2$—;
$R^{11}$ is selected from H or $C_{1-4}$ aliphatic; and
$Y^-$ is selected from the group consisting of fluoride, chloride, bromide, iodide, sulfate, nitrate, bicarbonate, carbonate, acetate, citrate, malonate, tartarate, succinate, benzoate, ascorbate, alpha-ketoglutarate, alpha-glycerophosphate, methylsulfonate,
toluenesulfonate, and benzenesulfonate; or
a pharmaceutically acceptable salt thereof.

4. The method of claim 1 wherein Z is —$CH_2$—$NR^1R^2$.
5. The method of claim 4 wherein $R^1$ and $R^2$ are independently selected from hydrogen, —CN or optionally substituted $C_1$-$C_4$ alkyl.
6. The method of claim 5 wherein $R^1$ and $R^2$ are independently selected from —$NO_2$, —CN, —$CH_3$, —$CF_3$, —$CH_2CH_3$, —$CH_2CF_3$, —$CH_2Cl$, —$CH_2OH$, —$CH_2CH_2OH$ and —$CH_2NH_2$.
7. The method of claim 4 wherein $R^1$ and $R^2$ together with N form an optionally substituted ring.
8. The method of claim 7 wherein said ring is a monocyclic, bicyclic or tricyclic alkyl or aryl ring system, said ring system optionally substituted and optionally comprising one or more heteroatoms or a group selected from —CO—, —SO—, and —$SO_2$.
9. The method of claim 8 wherein $R^1$ and $R^2$ are —$CH_2$($CH_2)_n CH_2Y$—; where Y is a heteroatom or a group selected from —CO—, —SO—, and —$SO_2$—; n is an integer 0 to 5; and together with N form an optionally substituted ring, said ring optionally fused to a cycloalkyl or aryl group to form a bicyclic or tricyclic ring system, said system optionally substituted and optionally comprising one or more heteroatoms.
10. The method of claim 8 wherein $R_1$ and $R_2$ are —$(CH_2)_a$—Y—$(CH_2)_b$—;
where Y is a heteroatom or a group selected from —CO—, —SO—, and —$SO_2$—; a is an integer 0 to 5; b is an integer 0 to 5; the sum of a and b being 0 to 5; and together with N form an optionally substituted ring, said ring optionally fused to a cycloalkyl or aryl group to form a bicyclic or tricyclic ring system, said system optionally substituted and optionally comprising one or more heteroatoms.
11. The method of claim 8 wherein $NR_1R_2$ is selected from optionally substituted aziridin-1-yl, azetidin-1-yl, pyrrolidin-1-yl, piperidin-1-yl, homopiperidyn-1-yl and heptamethyleneimin-1-yl.
12. The method of claim 1 wherein the compound of formula (I) is selected from:
11S, 11,13-Dihydro,13-dimethylaminoparthenolide;
11S, 11,13-Dihydro,13-diethylaminoparthenolide;
11S, 11,13-Dihydro,13-(tert-butylamino)parthenolide;
11S, 11,13-Dihydro,13-(pyrrolidin-1-yl)parthenolide;
11S, 11,13-Dihydro,13-(piperidin-1-yl)parthenolide;
11S, 11,13-Dihydro,13-(morpholin-1-yl)parthenolide;
11S, 11,13-Dihydro,13-(4-methylpiperidin-1-yl)parthenolide;
11S, 11,13-Dihydro,13-(4-methylpiperazin-1-yl)parthenolide;
11S, 11,13-Dihydro,13-(homopiperidin-1-yl)parthenolide;
11S, 11,13-Dihydro, 13-(heptamethyleneimin-1-yl)parthenolide;
11S, 11,13-Dihydro,13-(azetidin-1-yl)parthenolide;
11S, 11,13-Dihydro,13-methylbutyl aminoparthenolide;
11S, 11,13-Dihydro,13-methyl pentyl aminoparthenolide;
11S, 11,13-Dihydro,13-ethylaminoparthenolide;
11S, 11,13-Dihydro,13-methylaminoparthenolide;
11S, 11,13-Dihydro,13-cyclopropylaminoparthenolide;
11S, 11,13-Dihydro,13-propargylaminoparthenolide;
11S, 11,13-Dihydro,13-(N-benzyl-N-ethylamine)parthenolide;
11S, 11,13-Dihydro,13-(N-prolyl)parthenolide;
11S, 11,13-Dihydro,13-(S-thiophenolyl)parthenolide;
11S, 11,13-Dihydro,13-(N,N-diethanolamine)parthenolide;
11S, 11,13-Dihydro,13-(thiomorpholin-4-yl)parthenolide;
11S, 11,13-Dihydro,13-(4-hydroxypiperidin-1-yl)parthenolide;
11S, 11,13-Dihydro,13-(1-methylhomopiperizin-4-yl) parthenolide;
11S, 11,13-Dihydro,13-(S-mercaptoacetyl)parthenolide;
11S, 11,13-Dihydro,13-(4-(2'-hydroxyethyl)piperidin-1-yl)parthenolide;
11S, 11,13-Dihydro,13-(piperazin-1-yl-4-carboxaldehyde)parthenolide;
11S, 11,13-Dihydro,13-(4-benzylpiperidin-1-yl)parthenolide;
11S, 11,13-Dihydro,13-(piperidin-1-yl-4-carboxylic acid) parthenolide;
11S, 11,13-Dihydro,13-(azetidin-1-yl-3-carboxylic acid) parthenolide;
11S, 11,13-Dihydro,13-(S-cysteinyl)parthenolide;
11S, 11,13-Dihydro,13-(4-(piperidin-1'-yl)piperidin-1-yl))parthenolide;
11S, 11,13-Dihydro,13-diallylaminoparthenolide; or
a pharmaceutically acceptable salt thereof.

13. The method of claim 12 wherein the compound of formula (I) is
11S, 11,13-Dihydro,13-dimethylaminoparthenolide; or a pharmaceutically acceptable salt thereof.

14. The method of claim 13 wherein the compound of formula (I) is
11S, 11,13-Dihydro,13-dimethylaminoparthenolide hydrochloride; or
11S, 11,13-Dihydro,13-dimethylaminoparthenolide maleate.

15. The method of claim 1 wherein the compound of formula (I) is selected from:
11S, 11,13-Dihydro,13-(pyrrolidin-1-yl)parthenolide hydrochloride;
11S, 11,13-Dihydro,13-(piperidin-1-yl)parthenolide hydrochloride;
11S, 11,13-Dihydro,13-(4-methylpiperidin-1-yl)parthenolide hydrochloride;
11S, 11,13-Dihydro,13-dimethylaminoparthenolide methiodide; or
11S, 11,13-Dihydro,13-(4-methylpiperidin-1-yl)parthenolide methiodide.

16. The method of claim 1 wherein Z is —$CH_2$S—$R^1$; wherein
$R^1$ is selected from optionally substituted straight-chained or branched aliphatic wherein optional substituents are selected from one or more of —$NH_2$, —$N(C_{1-4}$ aliphatic$)_2$, halogen, —OH, —O—($C_{1-4}$ aliphatic), —$NO_2$, —CN, —$CO_2$H, —$CO_2(C_{1-4}$ aliphatic), —O—(halo $C_{1-4}$ aliphatic), or -(halo $C_{1-4}$ aliphatic); wherein each $C_{1-4}$ aliphatic is optionally substituted; cycloalkyl, heterocycloalkyl, aryl or heteroaryl.

17. The method of claim 2 wherein Z is —$CH_2$—$NR^1R^2$.

18. The method of claim 17 wherein $R^1$ and $R^2$ are independently selected from hydrogen, —CN or optionally substituted $C_1$-$C_4$ alkyl.

19. The method of claim 18 wherein $R^1$ and $R^2$ are independently selected from —$NO_2$, —CN, —$CH_3$, —$CF_3$, —$CH_2CH_3$, —$CH_2CF_3$, —$CH_2$Cl, —$CH_2$OH, —$CH_2CH_2$OH and —$CH_2NH_2$.

20. The method of claim 17 wherein $R^1$ and $R^2$ together with N form an optionally substituted ring.

21. The method of claim 20 wherein said ring is a monocyclic, bicyclic or tricyclic alkyl or aryl ring system, said ring system optionally substituted and optionally comprising one or more heteroatoms or a group selected from —CO—, —SO—, and —$SO_2$.

22. The method of claim 21 wherein $R^1$ and $R^2$ are —$CH_2$($CH_2$)$_n$$CH_2$Y—; where Y is a heteroatom or a group selected from —CO—, —SO—, and —$SO_2$—; n is an integer 0 to 5; and together with N form an optionally substituted ring, said ring optionally fused to a cycloalkyl or aryl group to form a bicyclic or tricyclic ring system, said system optionally substituted and optionally comprising one or more heteroatoms.

23. The method of claim 21 wherein $R_1$ and $R_2$ are —($CH_2$)$_a$—Y—($CH_2$)$_b$—;
where Y is a heteroatom or a group selected from —CO—, —SO—, and —$SO_2$—; a is an integer 0 to 5; b is an integer 0 to 5; the sum of a and b being 0 to 5; and together with N form an optionally substituted ring, said ring optionally fused to a cycloalkyl or aryl group to form a bicyclic or tricyclic ring system, said system optionally substituted and optionally comprising one or more heteroatoms.

24. The method of claim 21 wherein $NR_1R_2$ is selected from optionally substituted aziridin-1-yl, azetidin-1-yl, pyrrolidin-1-yl, piperidin-1-yl, homopiperidyn-1-yl and heptamethyleneimin-1-yl.

25. The method of claim 2 wherein the compound of formula (I) is selected from:
11S, 11,13-Dihydro,13-dimethylaminoparthenolide;
11S, 11,13-Dihydro,13-diethylaminoparthenolide;
11S, 11,13-Dihydro,13-(tert-butylamino)parthenolide;
11S, 11,13-Dihydro,13-(pyrrolidin-1-yl)parthenolide;
11S, 11,13-Dihydro,13-(piperidin-1-yl)parthenolide;
11S, 11,13-Dihydro,13-(morpholin-1-yl)parthenolide;
11S, 11,13-Dihydro,13-(4-methylpiperidin-1-yl)parthenolide;
11S, 11,13-Dihydro,13-(4-methylpiperazin-1-yl)parthenolide;
11S, 11,13-Dihydro,13-(homopiperidin-1-yl)parthenolide;
11S, 11,13-Dihydro, 13-(heptamethyleneimin-1-yl)parthenolide;
11S, 11,13-Dihydro,13-(azetidin-1-yl)parthenolide;
11S, 11,13-Dihydro,13-methylbutyl aminoparthenolide;
11S, 11,13-Dihydro,13-methyl pentyl aminoparthenolide;
11S, 11,13-Dihydro,13-ethylaminoparthenolide;
11S, 11,13-Dihydro,13-methylaminoparthenolide;
11S, 11,13-Dihydro,13-cyclopropylaminoparthenolide;
11S, 11,13-Dihydro,13-propargylaminoparthenolide;
11S, 11,13-Dihydro,13-(N-benzyl-N-ethylamine)parthenolide;
11S, 11,13-Dihydro,13-(N-prolyl)parthenolide;
11S, 11,13-Dihydro,13-(S-thiophenolyl)parthenolide;
11S, 11,13-Dihydro,13-(N,N-diethanolamine)parthenolide;
11S, 11,13-Dihydro,13-(thiomorpholin-4-yl)parthenolide;
11S, 11,13-Dihydro,13-(4-hydroxypiperidin-1-yl)parthenolide;
11S, 11,13-Dihydro,13-(1-methylhomopiperizin-4-yl)parthenolide;
11S, 11,13-Dihydro,13-(S-mercaptoacetyl)parthenolide;
11S, 11,13-Dihydro,13-(4-(2'-hydroxyethyl)piperidin-1-yl)parthenolide;
11S, 11,13-Dihydro,13-(piperazin-1-yl-4-carboxaldehyde)parthenolide;
11S, 11,13-Dihydro,13-(4-benzylpiperidin-1-yl)parthenolide;
11S, 11,13-Dihydro,13-(piperidin-1-yl-4-carboxylic acid) parthenolide;
11S, 11,13-Dihydro,13-(azetidin-1-yl-3-carboxylic acid) parthenolide;
11S, 11,13-Dihydro,13-(S-cysteinyl)parthenolide;
11S, 11,13-Dihydro,13-(4-(piperidin-1'-yl)piperidin-1-yl))parthenolide;
11S, 11,13-Dihydro,13-diallylaminoparthenolide; or
a pharmaceutically acceptable salt thereof.

26. The method of claim 25 wherein the compound of formula (I) is
11S, 11,13-Dihydro,13-dimethylaminoparthenolide; or
a pharmaceutically acceptable salt thereof.

27. The method of claim 26 wherein the compound of formula (I) is
11S, 11,13-Dihydro,13-dimethylaminoparthenolide hydrochloride; or
11S, 11,13-Dihydro,13-dimethylaminoparthenolide maleate.

28. The method of claim 2 wherein the compound of formula (I) is selected from:

11S, 11,13-Dihydro,13-(pyrrolidin-1-yl)parthenolide hydrochloride;
11S, 11,13-Dihydro,13-(piperidin-1-yl)parthenolide hydrochloride;
11S, 11,13-Dihydro,13-(4-methylpiperidin-1-yl)parthenolide hydrochloride;
11S, 11,13-Dihydro,13-dimethylaminoparthenolide methiodide; or
11S, 11,13-Dihydro,13-(4-methylpiperidin-1-yl)parthenolide methiodide.

29. The method of claim 2 wherein Z is —CH$_2$S—R$^1$; wherein R$^1$ is selected from optionally substituted straight-chained or branched aliphatic wherein optional substituents are selected from one or more of —NH$_2$, —N(C$_{1-4}$ aliphatic)$_2$, halogen, —OH, —O—(C$_{1-4}$ aliphatic), —NO$_2$, —CN, —CO$_2$H, —CO$_2$(C$_{1-4}$ aliphatic), —O—(halo C$_{1-4}$ aliphatic), or -(halo C$_{1-4}$ aliphatic); wherein each C$_{1-4}$ aliphatic is optionally substituted; cycloalkyl, heterocycloalkyl, aryl or heteroaryl.

30. The method of claim 2 wherein Z is —CH$_2$S—R$^1$; wherein
R$^1$ is selected from optionally substituted straight-chained or branched aliphatic wherein optional substituents are selected from one or more of —NH$_2$, —N(C$_{1-4}$ aliphatic)$_2$, halogen, —OH, —O—(C$_{1-4}$ aliphatic), —NO$_2$, —CN, —CO$_2$H, —CO$_2$(C$_{1-4}$ aliphatic), —O—(halo C$_{1-4}$ aliphatic), or -(halo C$_{1-4}$ aliphatic); wherein each C$_{1-4}$ aliphatic is optionally substituted;
cycloalkyl, heterocycloalkyl, aryl or heteroaryl.

31. The method of claim 3 wherein Z is —CH$_2$—NR$^1$R$^2$.

32. The method of claim 31 wherein R$^1$ and R$^2$ are independently selected from hydrogen, —CN or optionally substituted C$_1$-C$_4$ alkyl.

33. The method of claim 32 wherein R$^1$ and R$^2$ are independently selected from —NO$_2$, —CN, —CH$_3$, —CF$_3$, —CH$_2$CH$_3$, —CH$_2$CF$_3$, —CH$_2$Cl, —CH$_2$OH, —CH$_2$CH$_2$OH and —CH$_2$NH$_2$.

34. The method of claim 31 wherein R$^1$ and R$^2$ together with N form an optionally substituted ring.

35. The method of claim 34 wherein said ring is a monocyclic, bicyclic or tricyclic alkyl or aryl ring system, said ring system optionally substituted and optionally comprising one or more heteroatoms or a group selected from —CO—, —SO—, and —SO$_2$.

36. The method of claim 35 wherein R$^1$ and R$^2$ are —CH$_2$(CH$_2$)$_n$CH$_2$Y—; where Y is a heteroatom or a group selected from —CO—, —SO—, and —SO$_2$—; n is an integer 0 to 5; and together with N form an optionally substituted ring, said ring optionally fused to a cycloalkyl or aryl group to form a bicyclic or tricyclic ring system, said system optionally substituted and optionally comprising one or more heteroatoms.

37. The method of claim 35 wherein R$_1$ and R$_2$ are —(CH$_2$)$_a$—Y—(CH$_2$)$_b$—;
where Y is a heteroatom or a group selected from —CO—, —SO—, and —SO$_2$—; a is an integer 0 to 5; b is an integer 0 to 5; the sum of a and b being 0 to 5; and together with N form an optionally substituted ring, said ring optionally fused to a cycloalkyl or aryl group to form a bicyclic or tricyclic ring system, said system optionally substituted and optionally comprising one or more heteroatoms.

38. The method of claim 35 wherein NR$_1$R$_2$ is selected from optionally substituted aziridin-1-yl, azetidin-1-yl, pyrrolidin-1-yl, piperidin-1-yl, homopiperidyn-1-yl and heptamethyleneimin-1-yl.

39. The method of claim 3 wherein the compound of formula (I) is selected from:
11S, 11,13-Dihydro,13-dimethylaminoparthenolide;
11S, 11,13-Dihydro,13-diethylaminoparthenolide;
11S, 11,13-Dihydro,13-(tert-butylamino)parthenolide;
11S, 11,13-Dihydro,13-(pyrrolidin-1-yl)parthenolide;
11S, 11,13-Dihydro,13-(piperidin-1-yl)parthenolide;
11S, 11,13-Dihydro,13-(morpholin-1-yl)parthenolide;
11S, 11,13-Dihydro,13-(4-methylpiperidin-1-yl)parthenolide;
11S, 11,13-Dihydro,13-(4-methylpiperazin-1-yl)parthenolide;
11S, 11,13-Dihydro,13-(homopiperidin-1-yl)parthenolide;
11S, 11,13-Dihydro, 13-(heptamethyleneimin-1-yl)parthenolide;
11S, 11,13-Dihydro,13-(azetidin-1-yl)parthenolide;
11S, 11,13-Dihydro,13-methylbutyl aminoparthenolide;
11S, 11,13-Dihydro,13-methyl pentyl aminoparthenolide;
11S, 11,13-Dihydro,13-ethylaminoparthenolide;
11S, 11,13-Dihydro,13-methylaminoparthenolide;
11S, 11,13-Dihydro,13-cyclopropylaminoparthenolide;
11S, 11,13-Dihydro,13-propargylaminoparthenolide;
11S, 11,13-Dihydro,13-(N-benzyl-N-ethylamine)parthenolide;
11S, 11,13-Dihydro,13-(N-prolyl)parthenolide;
11S, 11,13-Dihydro,13-(S-thiophenolyl)parthenolide;
11S, 11,13-Dihydro,13-(N,N-diethanolamine)parthenolide;
11S, 11,13-Dihydro,13-(thiomorpholin-4-yl)parthenolide;
11S, 11,13-Dihydro,13-(4-hydroxypiperidin-1-yl)parthenolide;
11S, 11,13-Dihydro,13-(1-methylhomopiperizin-4-yl)parthenolide;
11S, 11,13-Dihydro,13-(S-mercaptoacetyl)parthenolide;
11S, 11,13-Dihydro,13-(4-(2'-hydroxyethyl)piperidin-1-yl)parthenolide;
11S, 11,13-Dihydro,13-(piperazin-1-yl-4-carboxaldehyde)parthenolide;
11S, 11,13-Dihydro,13-(4-benzylpiperidin-1-yl)parthenolide;
11S, 11,13-Dihydro,13-(piperidin-1-yl-4-carboxylic acid)parthenolide;
11S, 11,13-Dihydro,13-(azetidin-1-yl-3-carboxylic acid)parthenolide;
11S, 11,13-Dihydro,13-(S-cysteinyl)parthenolide;
11S, 11,13-Dihydro,13-(4-(piperidin-1'-yl)piperidin-1-yl))parthenolide;
11S, 11,13-Dihydro,13-diallylaminoparthenolide; or
a pharmaceutically acceptable salt thereof.

40. The method of claim 39 wherein the compound of formula (I) is
11S, 11,13-Dihydro,13-dimethylaminoparthenolide; or
a pharmaceutically acceptable salt thereof.

41. The method of claim 40 wherein the compound of formula (I) is
11S, 11,13-Dihydro,13-dimethylaminoparthenolide hydrochloride; or
11S, 11,13-Dihydro,13-dimethylaminoparthenolide maleate.

42. The method of claim 3 wherein the compound of formula (I) is selected from:
11S, 11,13-Dihydro,13-(pyrrolidin-1-yl)parthenolide hydrochloride;
11S, 11,13-Dihydro,13-(piperidin-1-yl)parthenolide hydrochloride;
11S, 11,13-Dihydro,13-(4-methylpiperidin-1-yl)parthenolide hydrochloride;

11S, 11,13-Dihydro,13-dimethylaminoparthenolide methiodide; or 11S, 11,13-Dihydro,13-(4-methylpiperidin-1-yl)parthenolide methiodide.

43. The method of claim 3 wherein Z is —CH$_2$S—R$^1$; wherein

R$^1$ is selected from optionally substituted straight-chained or branched aliphatic wherein optional substituents are selected from one or more of —NH$_2$, —N(C$_{1-4}$ aliphatic)$_2$, halogen, —OH, —O—(C$_{1-4}$ aliphatic), —NO$_2$, —CN, —CO$_2$H, —CO$_2$(C$_{1-4}$ aliphatic), —O—(halo C$_{1-4}$ aliphatic), or -(halo C$_{1-4}$ aliphatic); wherein each C$_{1-4}$ aliphatic is optionally substituted; cycloalkyl, heterocycloalkyl, aryl or heteroaryl.

* * * * *